(12) United States Patent
Gordon et al.

(10) Patent No.: US 9,533,118 B2
(45) Date of Patent: Jan. 3, 2017

(54) SYSTEMS AND METHODS FOR DRIVING NEBULIZERS

(71) Applicant: Nektar Therapeutics, San Francisco, CA (US)

(72) Inventors: Benjamin Morris Gordon, Cambridge (GB); Steven David Gardner, Yaxley (GB); Matthew James Hayes, Cambridge (GB)

(73) Assignee: Nektar Therapeutics, San Francisco, CA (US)

( * ) Notice: Subject to any disclaimer, the term of this patent is extended or adjusted under 35 U.S.C. 154(b) by 352 days.

(21) Appl. No.: 14/017,531

(22) Filed: Sep. 4, 2013

(65) Prior Publication Data

US 2014/0007864 A1    Jan. 9, 2014

Related U.S. Application Data

(63) Continuation-in-part of application No. 13/384,579, filed as application No. PCT/US2010/042473 on Jul. 19, 2010, now Pat. No. 9,149,588.
(Continued)

(51) Int. Cl.
*B05B 1/08* (2006.01)
*A61M 16/14* (2006.01)
(Continued)

(52) U.S. Cl.
CPC ............ *A61M 16/14* (2013.01); *A61M 11/005* (2013.01); *A61M 15/0085* (2013.01);
(Continued)

(58) Field of Classification Search
CPC .................... A61M 16/0833; A61M 16/0066; A61M 2205/8206; A61M 2016/0024; A61M 16/14; A61M 15/0085; A61M 11/005; B05B 17/0646
(Continued)

(56) References Cited

U.S. PATENT DOCUMENTS 3,819,961 A    6/1974 Verlet et al.
5,349,852 A    9/1994 Kamen et al.
(Continued)

FOREIGN PATENT DOCUMENTS

AU    2010273957 A1    2/2012
CA    2768487 A1    1/2011
(Continued)

OTHER PUBLICATIONS

Office Action in related Eurasian application No. 201200134 issued on Apr. 24, 2014, 3 pages.
(Continued)

*Primary Examiner* — Jason Boeckmann
(74) *Attorney, Agent, or Firm* — Kilpatrick Townsend & Stockton LLP

(57) ABSTRACT

In various arrangements, a nebulizer element of a nebulizer may be energized with a drive signal. A phase offset of the drive signal may be measured. A phase delta may be determined. The phase delta may indicate a difference between a target phase offset and the measured phase offset. The target phase offset may indicate a non-zero target phase difference between the voltage of the drive signal and the current of the drive signal. A frequency of the drive signal may be changed to decrease the phase delta.

21 Claims, 12 Drawing Sheets

Related U.S. Application Data

(60) Provisional application No. 61/226,591, filed on Jul. 17, 2009.

(51) Int. Cl.
*A61M 16/00* (2006.01)
*A61M 11/00* (2006.01)
*A61M 15/00* (2006.01)
*A61M 16/08* (2006.01)

(52) U.S. Cl.
CPC .... *A61M 16/0057* (2013.01); *A61M 16/0833* (2014.02); *A61M 16/0066* (2013.01); *A61M 2016/0024* (2013.01); *A61M 2205/8206* (2013.01)

(58) Field of Classification Search
USPC ............................ 239/102.1, 102.2; 700/280
See application file for complete search history.

(56) References Cited

U.S. PATENT DOCUMENTS

| | | | |
|---|---|---|---|
| 5,853,665 | A | 12/1998 | Ade et al. |
| 6,569,109 | B2 | 5/2003 | Sakurai et al. |
| 6,978,779 | B2 | 12/2005 | Haveri |
| 6,983,747 | B2 | 1/2006 | Gallem et al. |
| 7,155,980 | B2 | 1/2007 | Kurtz |
| 7,197,948 | B2 | 4/2007 | Sander |
| 8,115,366 | B2 | 2/2012 | Hoffman et al. |
| 8,616,195 | B2 | 12/2013 | Power et al. |
| 2001/0039389 | A1 | 11/2001 | Sakurai et al. |
| 2002/0129813 | A1 | 9/2002 | Litherland et al. |
| 2003/0196660 | A1 | 10/2003 | Haveri |
| 2005/0224076 | A1 | 10/2005 | Pfichner et al. |
| 2006/0090576 | A1 | 5/2006 | Sander |
| 2006/0102172 | A1 | 5/2006 | Feiner et al. |
| 2006/0150740 | A1 | 7/2006 | Kurtz |
| 2007/0015281 | A1 | 1/2007 | Bebee |
| 2007/0152081 | A1 | 7/2007 | Chou et al. |
| 2012/0111963 | A1 | 5/2012 | Gordon et al. |

FOREIGN PATENT DOCUMENTS

| | | |
|---|---|---|
| CN | 102573745 A | 7/2012 |
| EA | 201200134 A1 | 8/2012 |
| EP | 2453864 A1 | 5/2012 |
| IN | 15/2015 A | 4/2015 |
| JP | H05-261324 A | 10/1993 |
| JP | 2012533367 A | 12/2012 |
| KR | 10-2012-0052997 A | 5/2012 |
| MX | 2012000751 A | 5/2012 |
| TW | I294791 | 3/2008 |
| WO | 2011/009133 A1 | 1/2011 |
| WO | 2015/034480 A1 | 3/2015 |

OTHER PUBLICATIONS

Extended European Search Report of PCT/US2010/042473 mailed on Aug. 28, 2014, 17 pages.
Eurasian Office Action mailed on Oct. 30, 2014 for Eurasian Application No. 201200134 filed on Jul. 19, 2010, all pages.
Chinese Office Action mailed on Oct. 31, 2014 for Chinese Application No. 201080036580.X filed on Jul. 19, 2010, all pages.
Australian Office Action mailed on Nov. 27, 2014 for Australian Application No. 2010273957 filed on Jul. 19, 2010, all pages.
Israeli Office Action mailed on Dec. 4, 2014 for Israeli Application No. 217512 filed on Jul. 19, 2010, all pages.
Office action in Chinese Application No. 201080036580 issued on Jun. 13, 2014. 5 pages.
International Search Report and Written Opinion of related PCT/US2013/058004 mailed on Jul. 7, 2014, 141 pages.
Office action in Japanese Application No. 553851 issued on Jul. 15, 2014, 3 pages.
Office action in Mexican Application No. 553853 issued on Jul. 7, 2014, 2 pages.
International Search Report and Written Opinion mailed Sep. 15, 2010 for PCT/US2010/042473 filed Jul. 19, 2010.
Chinese First Office Action issued on Oct. 8, 2013 for Chinese Patent Application No. CN201080036580.X filed on Jul. 19, 2010, all pages.
Eurasian Office Action issued on Oct. 15, 2013 for Eurasian Patent Application No. EA201200134 filed on Jul. 19, 2010, all pages.
Japanese Office Action issued on Apr. 21, 2015 for Korean Patent Application No. JP2012-520838 filed on Jul. 19, 2010, all pages. (Not Translated).
International Preliminary Report on Patentability issued on Jan. 17, 2012 for International Patent Application No. PCT/US2010/042473 filed on Jul. 19, 2010, all pages.
Non-Final Office Action dated Sep. 9, 2014 for U.S. Appl. No. 13/384,579, filed Jan. 17, 2012, all pages.
Final Office Action dated Mar. 18, 2015 for U.S. Appl. No. 13/384,579, filed Jan. 17, 2012, all pages.
International Preliminary Report on Patentability of PCT/US2013/058004 mailed Mar. 17, 2016, all pages.
International Search Report and Written Opinion of PCT/US2013/058004 mailed Mar. 17, 2016, all pages.

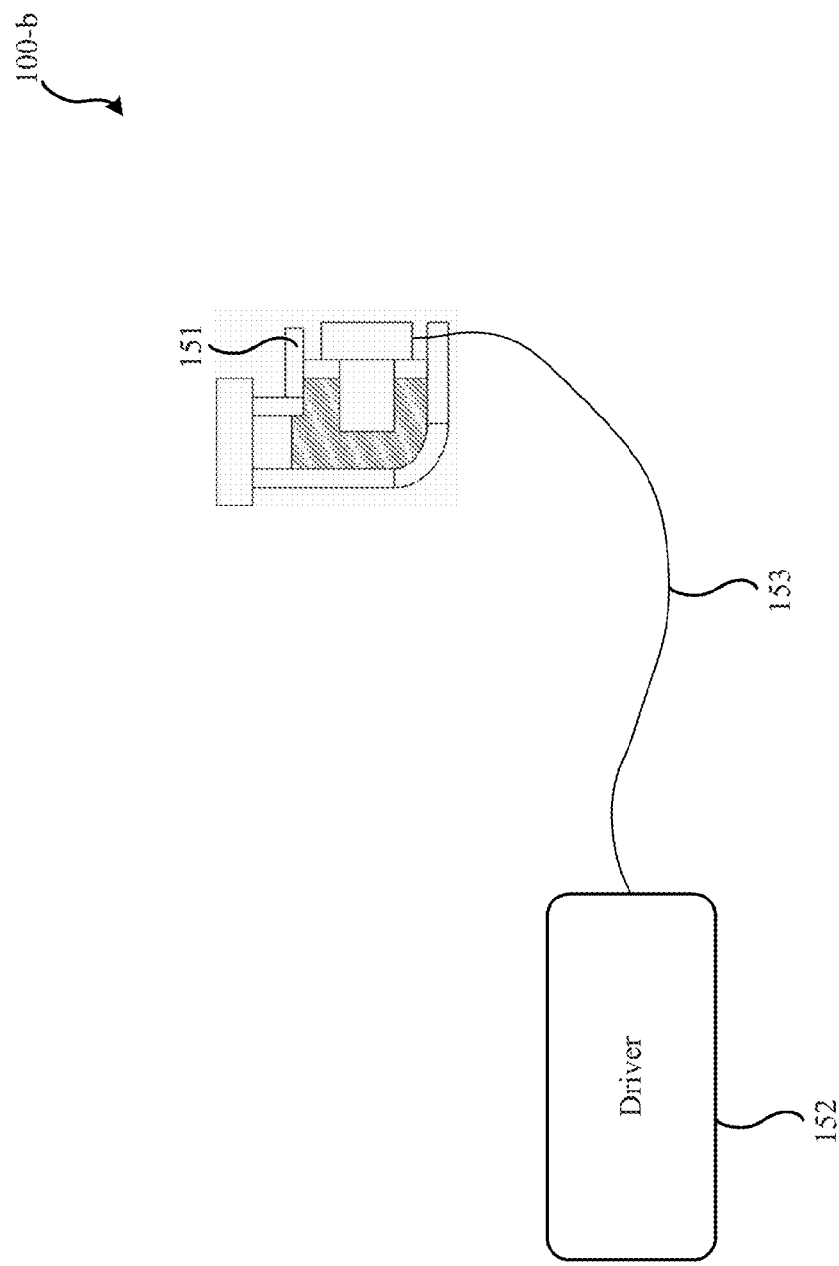

SYSTEMS AND METHODS FOR DRIVING NEBULIZERS

CROSS-REFERENCES TO RELATED APPLICATIONS

This Application is a continuation-in-part of U.S. application Ser. No. 13/384,579, filed Jan. 17, 2012, entitled "Systems and Methods for Driving Sealed Nebulizers," which is hereby incorporated by reference for all purposes.

U.S. application Ser. No. 13/384,579 claims the benefit of U.S. Provisional Patent Application No. 61/226,591, filed Jul. 17, 2009, entitled "Systems and Methods for Driving Sealed Nebulizers," and of International Application US/2010/042473, filed Jul. 19, 2010, entitled "Systems and Methods for Driving Sealed Nebulizers," the entire disclosures of both applications are hereby incorporated by reference for all purposes.

BACKGROUND

Embodiments of the present invention relate to nebulizers. In particular, the present invention relates to use of a variable frequency driver for a nebulizer.

A wide variety of procedures have been proposed to deliver a drug to a patient. In some drug delivery procedures the drug is a liquid and is dispensed in the form of fine liquid droplets for inhalation by a patient. A patient may inhale the drug for absorption through lung tissue. Further, the droplets forming the atomized mist may need to be very small to travel through small airways of the lungs. Such a mist may be formed by a nebulizer.

SUMMARY

In some embodiments, a method for driving a nebulizer element of a nebulizer is presented. The method may include energizing the nebulizer element of the nebulizer with a drive signal. The method may include measuring a phase offset of the drive signal. The phase offset may indicate a phase difference between a voltage of the drive signal and a current of the drive signal. The method may include, based on the measured phase offset of the drive signal, adjusting a frequency of the drive signal that energizes the nebulizer element such that the phase offset of the drive signal is maintained within a threshold range of a predefined phase offset.

Embodiments of such a method may involve one or more of the following: The method may include adjusting a voltage magnitude of the drive signal based on a change in frequency of the drive signal over time. The voltage magnitude may be adjusted based on a table of predetermined voltage magnitudes. The table may be selected based on a type of liquid stored in a reservoir of the nebulizer. Energizing the nebulizer element of the nebulizer with the drive signal may cause a liquid to be atomized. The liquid may be a medicine.

In some embodiments, the method for driving a nebulizer element of a nebulizer is presented. The method may include energizing the nebulizer element of the nebulizer with a drive signal. The method may include measuring a phase offset of the drive signal. The phase offset may indicate a phase difference between a voltage of the drive signal and a current of the drive signal. The method may include determining a phase delta. The phase delta may indicate a difference between a target phase offset and the measured phase offset. The target phase offset may indicate a non-zero target phase difference between the voltage of the drive signal and the current of the drive signal. The method may include changing a frequency of the drive signal to decrease the phase delta.

Embodiments of such a method may involve one or more of the following: Changing the frequency of the drive signal to decrease the phase delta value may include one or more of the following: changing the frequency of the drive signal to decrease the phase delta to less than a threshold phase delta in a high gain mode; determining the phase delta is less than the threshold phase delta; and at least partially in response to determining the phase delta is less than the first threshold phase delta, changing the frequency of the drive signal to decrease the phase delta in a low gain mode. The low gain mode may result in a smaller frequency change than the high gain mode.

Additionally or alternatively, embodiments of such a method may involve one or more of the following: The method may include measuring an impedance of the nebulizer element. Changing the frequency of the drive signal in the low gain mode is conditioned on the impedance of the nebulizer element not exceeding an impedance threshold. The method may include determining a slope of the phase offset. Changing the frequency of the drive signal in the low gain mode may be conditioned on the slope of the phase offset being negative. The phase delta threshold may be five degree or less. The method may include adjusting the voltage magnitude of the drive signal based on a change in frequency of the drive signal over time. The target phase offset between the voltage of the drive signal and the current of the drive signal may be between 25 degrees and 35 degrees. The target phase difference between the voltage of the drive signal and the current of the drive signal may be 30 degrees. Energizing the nebulizer element of the nebulizer with the drive signal may cause a liquid to be atomized. The liquid may be a medicine.

In some embodiments, a nebulizer system is presented. The nebulizer system may include a liquid reservoir that is adapted to hold a liquid that is to be atomized. The nebulizer system may include a nebulizer, comprising an element having a plurality of apertures. The element may be configured to vibrate to atomize liquid drained from the liquid reservoir. The element may be driven by a drive signal. The nebulizer system may include a driver. The driver may include a frequency generator. The driver may include a phase shift detector configured to measure a phase offset of the drive signal. The phase offset may indicate a phase difference between a voltage of the drive signal and a current of the drive signal. The driver may include a processor. The processor may be configured to determine a phase delta. The phase delta may indicate a difference between a target phase offset and the measured phase offset. The target phase offset may indicate a non-zero target phase difference between the voltage of the drive signal and the current of the drive signal. The processor may be configured to change a frequency of the drive signal output by the frequency generator to decrease the phase delta.

Embodiments of such a nebulizer system may include one or more of the following: The processor being configured to change the frequency of the drive signal output by the frequency generator to decrease the phase delta may include the processor being configured to: change the frequency of the drive signal output by the frequency generator to decrease the phase delta to less than a threshold phase delta in a high gain mode; determine the phase delta is less than the threshold phase delta; and at least partially in response to determining the phase delta is less than the first threshold phase delta, change the frequency of the drive signal output by the frequency generator to decrease the phase delta in a low gain mode. The low gain mode may result in a smaller frequency change than the high gain mode. The processor may be further configured to calculate an impedance of the nebulizer element. The processor changing the frequency of the drive signal output by the frequency generator in the low gain mode may be conditioned on the impedance of the nebulizer element being below an impedance threshold.

Additionally or Alternatively, embodiments of such a nebulizer system may include one or more of the following: The processor may be further configured to determine a slope of the phase offset. The processor changing the frequency of the drive signal output by the frequency generator in the low gain mode may be conditioned on the slope of the phase offset being negative. The phase delta threshold may be five degree or less. The processor may be further configured to adjust the voltage magnitude of the drive signal output by the driver based on a change in frequency of the drive signal over time. The target phase offset between the voltage of the drive signal and the current of the drive signal may be between 25 degrees and 35 degrees. The target phase difference between the voltage of the drive signal and the current of the drive signal may be 30 degrees. Energizing the nebulizer element of the nebulizer with the drive signal may cause a liquid to be atomized. The liquid may be a medicine.

BRIEF DESCRIPTION OF THE DRAWINGS

A further understanding of the nature and advantages of the present invention may be realized by reference to the following drawings. In the appended figures, similar components or features may have the same reference label. Further, various components of the same type may be distinguished by following the reference label by a second label that distinguishes among the similar components. If only the first reference label is used in the specification, the description is applicable to any one of the similar components having the same first reference label irrespective of the second reference label.

FIG. 1B illustrates a simplified embodiment of a nebulizer with a driver unit.

DETAILED DESCRIPTION

Figure 1A:
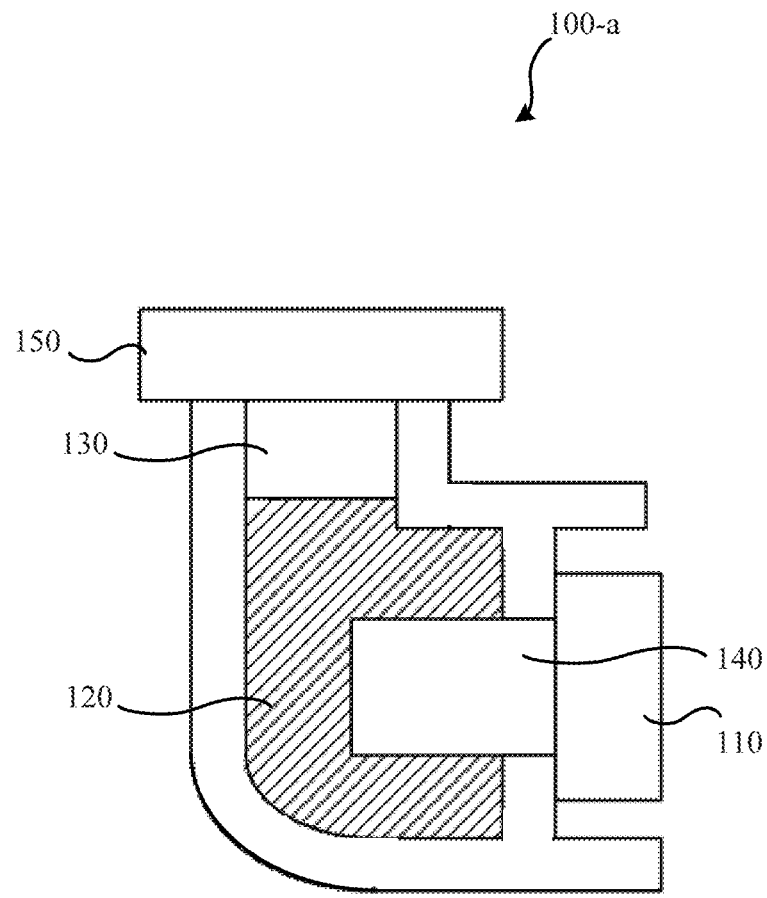
FIG. 1A illustrates a simplified embodiment of a nebulizer.

Devices, systems, and methods are described for the implementation of a novel architecture for driving a nebulizer. Various embodiments for driving nebulizers at the nebulizers' resonance frequencies or other off-resonance frequencies (possibly based on phase) are presented. In some embodiments, nebulizers with sealed drug reservoirs capable of developing a negative bias pressure (meaning the pressure within the reservoir is less than the pressure outside of the reservoir) as liquid is evacuated from the drug reservoir are presented. Embodiments detailed herein are also directed to driving a nebulizer element off-resonance such that a phase offset between the current and voltage of the signal used to drive the nebulizer element is maintained. For example, a non-zero phase offset between the current and voltage of the drive signal may be maintained such that a nebulizer element is driven at an off-resonance operating frequency. Various conditions involving the slope of the phase and/or the slope of the impedance (as the frequency of the drive signal is varied) may be required to be satisfied such that an operating frequency associated with a predefined phase offset is used to drive the nebulizer element. Additional conditions may additionally or alternatively need to be satisfied, such as maximum and/or minimum impedance thresholds.

By creating a negative bias pressure within the drug reservoir of a nebulizer, the efficiency of a nebulizer may be increased, thus allowing for higher liquid flow rates of liquid atomized, possibly with smaller and more consistent droplet sizes than in comparable conditions without a negative bias pressure. Such a negative bias pressure may be created by sealing the drug reservoir. As the liquid drug is drained from the drug reservoir (with little to no air entering to replace the drug's volume), a negative bias pressure, compared with the outside atmospheric pressure, may be created within the reservoir. While the negative bias pressure may assist in maintaining consistently sized droplets of mist, as the negative bias pressure decreases in pressure, the flow rate of liquid from the nebulizer may increase and/or a resonance frequency of the nebulizer element may shift.

An increased flow rate caused by a negative bias pressure may lead to the wrong dose of a medicine being delivered to a patient and/or the generation of improper droplet sizes. Such improper droplet sizes may alter how the droplets are absorbed into the human body. For example, if a patient inhales droplets that are too large, the droplets may not propagate into the deep lung tissue of the patient, but rather, the droplets may gather in the patient's larger airways. This may prevent proper absorption of the medicine's droplets by the patient.

Variances in flow rate may be additionally or alternatively caused by attempting to operate at or near a resonant frequency. While a first flow rate may be realized while the nebulizer element is being vibrated at a resonant frequency, if the resonant frequency of the nebulizer element changes, a second flow rate, which may be less than the first flow rate, may result when the nebulizer element is vibrated off-resonance. Therefore, if the nebulizer element vibrates at a resonant frequency, but the resonant frequency changes, the flow rate from the nebulizer element may be difficult to monitor, maintain, and/or predict.

Droplets may be created from a stored amount of liquid in the drug reservoir by a nebulizer element. The nebulizer element may have a number of small holes. When an electrical signal (referred to as the drive signal), such as a waveform, is applied to the nebulizer element, the nebulizer element may vibrate at or near the frequency of the waveform received. While vibrating, the nebulizer element may allow an amount of the liquid to pass through the holes on the element and form airborne droplets. The nebulizer element may function more efficiently and produce consistent droplet sizes when the nebulizer element is vibrating at or near a resonant frequency of the nebulizer element.

The nebulizer element may be driven near a resonant frequency or at some other off-resonance frequency. Driving near a resonant frequency or at some other frequency off-resonance, rather than at the resonant frequency, may result in desirable operating characteristics. Driving a nebulizer element off-resonance may provide a more consistent flow rate of atomized liquid than attempting to drive the nebulizer element on a resonant frequency. While driving directly on a resonant frequency of the nebulizer element may result in a higher flow rate of atomized liquid, it may be difficult to maintain vibration of the nebulizer element precisely on resonance due to changing factors, including of the amount of liquid in the reservoir decreasing during operation, the bias-pressure of the reservoir changing during operation, bubbles possibly forming on the nebulizer element, characteristics of the liquid being atomized, and/or the temperature of the nebulizer element varying. Such changing factors may result in one or more resonant frequencies of the nebulizer element increasing or decreasing. As such, a nebulizer element that is attempted to be driven at a resonant frequency may have a less predictable flow rate of atomized liquid due to the nebulizer element occasionally being driven off-resonance as the resonant frequency of the nebulizer element changes. Rather, a more predictable flow rate may be obtained by intentionally driving the nebulizer element off-resonance at an operating frequency with a constant or near constant phase offset between the current and voltage of the drive signal.

A nebulizer element may be considered driven at a resonant frequency when there is no phase offset between the current and voltage of the drive signal used to excite the nebulizer element. Driving the nebulizer element at an off-resonance frequency may be desirable for several reasons, including there being less variability in the flow rate of atomized liquid from the nebulizer element if the resonant frequency of the nebulizer element drifts (such as due to changing operating conditions of the nebulizer). At off-resonance frequencies, a phase offset between the current and voltage of the drive signal may be present. For example, driving a nebulizer element off-resonance with a phase offset of 30 degrees between the voltage waveform and the current waveform of the drive signal may produce a more consistent atomization flow rate than if the nebulizer element was attempted to be driven at a resonant frequency with no phase offset between the voltage and current of the drive signal. Maintaining an off-resonant frequency drive signal may be useful regardless of whether a sealed drug reservoir is used.

Referring to sealed drug reservoirs, as the negative bias pressure within the drug reservoir changes (e.g., a greater difference between the pressure inside the drug reservoir and the ambient pressure outside of the drug reservoir is formed), the resonant frequency of the nebulizer element may change. In order to maintain the nebulizer element vibrating at its resonant frequency, it may be necessary to change the frequency of the waveform used to drive the nebulizer element. Similarly, a frequency at which a particular offset between the voltage waveform and current waveform of the drive signal may vary as the negative bias pressure within the drug reservoir changes. In order to maintain the nebulizer element vibrating at the desired phase offset, it may be necessary to change the frequency of the waveform used to drive the nebulizer element.

Therefore, if a negative bias pressure occurs in the drug reservoir as liquid is drained during operation of the nebulizer, the frequency and magnitude of the waveform used to drive the nebulizer element may need to vary as the negative bias pressure within the drug reservoir changes in order to maintain efficient operation of the nebulizer element, including maintaining consistent dosing of the liquid drug and consistent droplet sizes.

To be clear, a sealed reservoir refers to a reservoir that prevents air from entering the reservoir as liquid is drained from the drug reservoir. It may, however, still be possible for air to enter the sealed drug reservoir through the holes in the nebulizer element. The greater the negative bias pressure (that is, the greater the difference between the pressure of the external environment and the pressure within the drug reservoir), the faster air may enter through holes in the nebulizer element.

FIG. 1A illustrates an embodiment of a possible nebulizer 100-a. The nebulizer 100-a may include a nebulizer element 110, a drug reservoir 120, a head space 130, an interface 140, and a cap 150. The nebulizer element 110 may be comprised of a piezoelectric ring that may expand and contract when an electric voltage is applied to the ring. The nebulizer element 110 may be a vibrating nebulizer element. The piezoelectric ring may be attached to a perforated membrane of the nebulizer element 110. Such a perforated membrane may have a number of holes passing through it. When an electric voltage is applied to the piezoelectric ring, this may cause the membrane to move and/or flex. Such movement of the membrane, while in contact with a liquid may cause the atomization (alternatively referred to as aerosolization) of the liquid.

A supply of a liquid, commonly a liquid drug, may be held in the drug reservoir 120. As illustrated, a drug reservoir is partially filled with a liquid drug. As the liquid drug is atomized, the amount of liquid drug remaining in the drug reservoir 120 may decrease. Depending on the amount of liquid drug in the drug reservoir 120, only a portion of the reservoir may be filled with liquid drug. The remaining portion of the drug reservoir 120 may be filled with gas, such as air. This space is commonly referred to as head space 130. An interface 140 may serve to transfer amounts of liquid drug between the drug reservoir 120 and the nebulizer element 110.

Nebulizers, and the techniques associated with such nebulizers, are described generally in U.S. Pat. Nos. 5,164,740; 5,938,117; 5,586,550; 5,758,637; 6,014,970; 6,085,740; 6,235,177; 6,615,824; 7,322,349, the complete disclosures of which are incorporated by reference for all purposes.

A nebulizer with a sealed drug reservoir may be part of a larger system. The embodiment of FIG. 1B illustrates such a nebulizer system 100-b. FIG. 1B illustrates a nebulizer 151 with a sealed drug reservoir connected to a driver 152. The sealed nebulizer illustrated in FIG. 1B may be the nebulizer of FIG. 1A, or may represent some other nebulizer. Driver 152 may control the rate and magnitude of vibration of the nebulizer element on nebulizer 151. Driver 152 may be connected to an element of nebulizer 151 via cable 153. Driver 152 may regulate the voltage and frequency of the signal provided to the nebulizer element of nebulizer 151. The regulation of the voltage and frequency of the signal may be based on the resonant frequency of the nebulizer element of nebulizer 151. Such a signal may vary depending on the magnitude of the negative bias pressure.

Figure 1C:
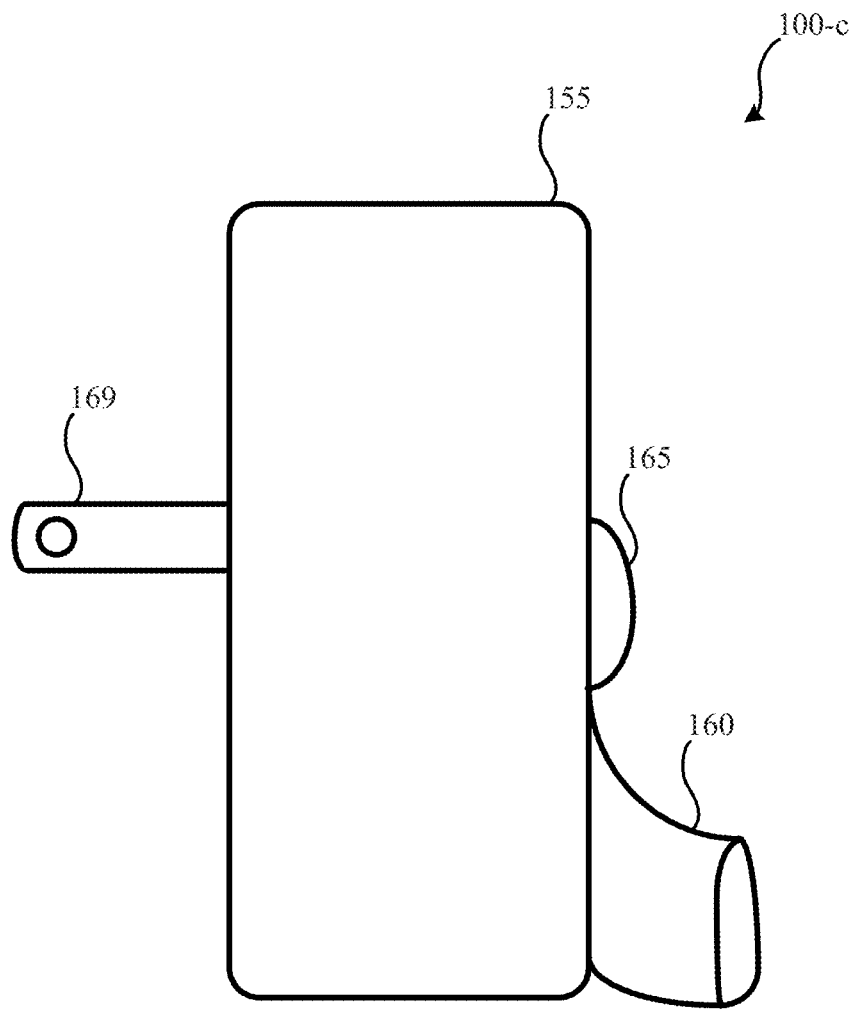
FIG. 1C illustrates a simplified embodiment of a handheld nebulizer with an integrated driver unit.

In some other embodiments of nebulizers, a driver may be incorporated into a handheld unit with the nebulizer. Nebulizer 100-c of FIG. 1C illustrates an embodiment of a handheld nebulizer with an integrated driver. Nebulizer 100-c may include a case 155, a mouthpiece 160, a trigger button 165, and an electrical plug 169. Case 155 may contain some or all of the elements found in other embodiments of nebulizers (such as nebulizer 100-a of FIG. 1A) and drivers (such as driver 152 of FIG. 1B). Therefore, contained within case 155 may be a sealed drug reservoir and/or a device capable of generating an electrical signal at a voltage magnitude and frequency to vibrate an element that atomizes liquid stored in the drug reservoir. A person receiving the atomized liquid drug may place her mouth on mouthpiece 160 and breathe in. While the person receiving the atomized liquid drug is breathing in, she may press trigger button 165 to trigger the element to begin aerosolizing liquid. In some embodiments, nebulizer 100-c may contain a sensor that detects when the person is breathing in and triggers the element to vibrate without trigger button 165 being necessary.

Nebulizer 100-c may also include an electrical plug 169. Electrical plug 169 may be connected to an electrical outlet to power nebulizer 100-c. Nebulizer 100-c may contain a battery, thereby allowing electrical plug 169 to be connected to an electrical outlet when nebulizer 100-c is not in use by a person, allowing a battery to be charged. Alternatively, in some embodiments of nebulizer 100-c, electrical plug 169 may need to be connected to an electrical outlet while nebulizer 100-c is in use by a person. In some embodiments, nebulizer 100-c may use replaceable batteries as its power source.

Figure 1D:
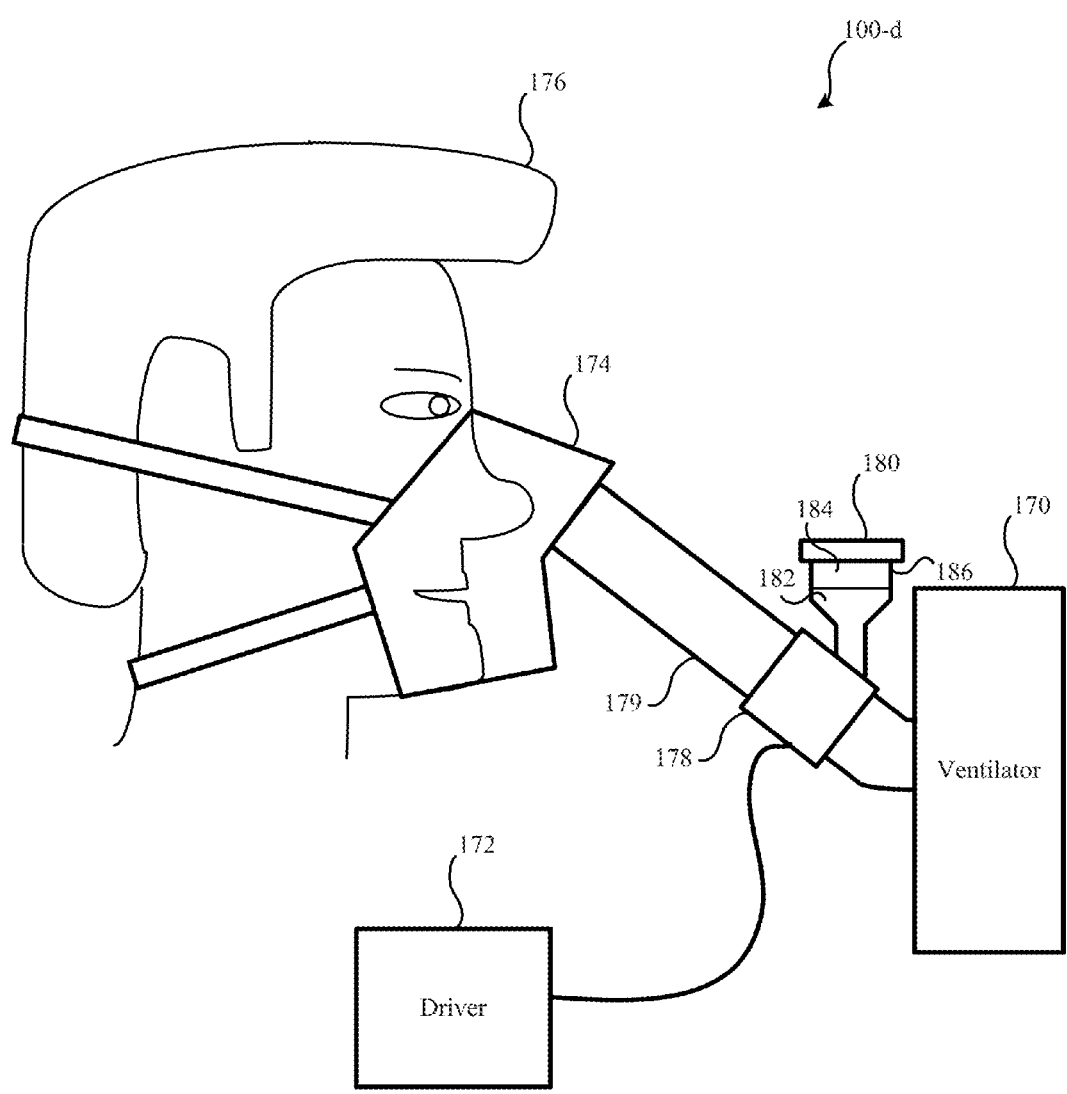
FIG. 1D illustrates a nebulizer integrated with a ventilator.

In some embodiments, a nebulizer may operate in conjunction with a ventilator. Nebulizer system 100-d in FIG. 1D illustrates a nebulizer 178 that supplies atomized liquid drug to a person 176 via a ventilator 170. Ventilator 170 may supply air suitable for breathing to person 176. Ventilator 170 may assist person 176 in breathing by forcing air into the lungs of person 176 and then releasing air to mimic breathing. While person 176 is using ventilator 170, it may be necessary to provide person 176 with atomized liquid, such as a liquid drug.

Nebulizer 178 may be connected to a drug reservoir 186 that is sealed by a cap 180. Drug reservoir 186 may contain an amount of liquid drug 182. This liquid drug may be delivered to nebulizer 178 as liquid drug is atomized by nebulizer 178. As liquid drug is atomized, liquid drug 182 may drain from drug reservoir 186, thereby increasing the volume of headspace 184. Headspace 184 may contain air. Headspace 184 may increase in volume, but may decrease in pressure as liquid drug 182 drains because drug reservoir 186 allows no or minimal air into headspace 184. In some embodiments, drug reservoir 186 may not be sealed; as such the pressure may remain constant.

Driver 172, which may represent the same driver as driver 152 of FIG. 1B (or may represent some other driver), may deliver a signal to nebulizer 178. This drive signal may control the vibration of an element of nebulizer 178. Nebulizer 178 may be attached to a tube 179 used to deliver air and atomized liquid drug to person 176. Tube 179 may terminate in a mask 174 covering the mouth and/or nose of person 176. The air and atomized liquid drug may then enter the airways of person 176.

Figure 2:
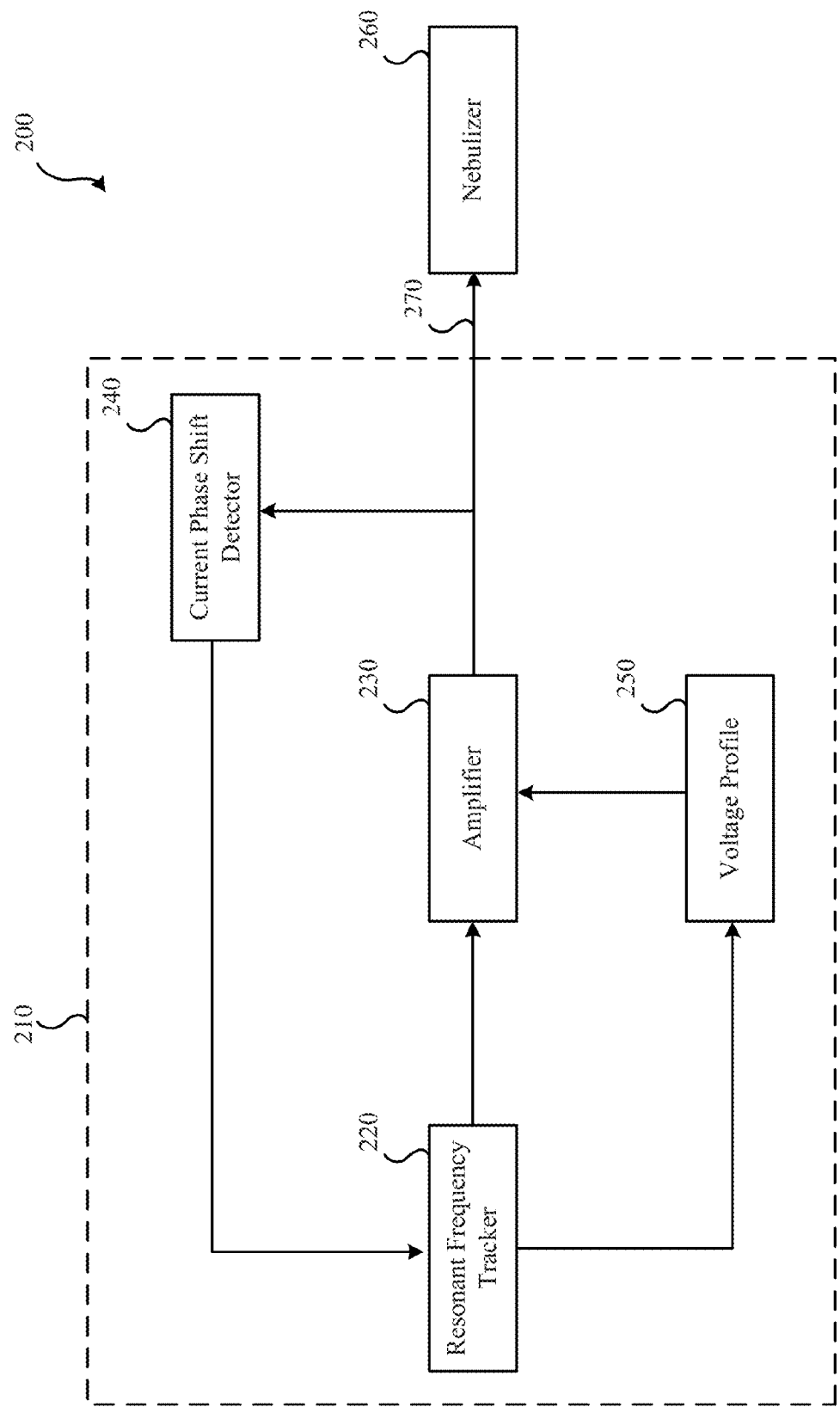
FIG. 2 illustrates a simplified embodiment of a driver coupled with a nebulizer.

A nebulizer, such as those illustrated in FIGS. 1A-1D, may be connected with a driver such as illustrated in FIG. 2.

FIG. 2 illustrates a simplified block diagram of a nebulizer system 200. The nebulizer 260 may be the nebulizer 100-a of FIG. 1A or may represent some other form of nebulizer such as those in the referenced applications or FIGS. 1B-1D. The nebulizer may be connected to the driver via a cable 270. Driver 210 may be driver 152 of FIG. 1B, or may be some other driver. Cable 270 may allow driver 210 to transmit an electrical waveform signal (the drive signal) of varying frequency and magnitude (of voltage) through cable 270 to drive an element of nebulizer 260.

Driver 210 may include an amplifier 230, a current phase shift detector 240, a resonant frequency tracker 220, and a voltage profile 250. Based upon the phase shift between the current supplied to nebulizer 260 and the voltage generated by amplifier 230, the nebulizer element's resonant frequency may be determined. From the resonant frequency, the negative bias pressure within the drug reservoir of the nebulizer may be determined, and the frequency and/or magnitude of the electrical waveform signal driving nebulizer 260 may be adjusted.

The determination of the resonant frequency may be accomplished using current phase shift detector 240. Current phase shift detector 240 monitors the phase shift between the phase of the current output by amplifier 230 to nebulizer 260 and the phase of the voltage output by amplifier 230 to nebulizer 260. Based upon the phase shift between the voltage and current observed by current phase shift detector 240, resonant frequency tracker 220 outputs an output waveform to amplifier 230 such that amplifier 230 outputs an electrical waveform signal with constant or near constant phase shift between the voltage and current of the electrical waveform signal driving the element of nebulizer 260. An electrical waveform signal with constant (or near constant) phase shift between the voltage and current of the electrical waveform signal may refer to the phase shift being held within a threshold range of the desired phase shift, such as +/−0.5 degrees or +/−1 degree. To maintain the constant or near constant phase shift, the frequency of the drive signal may need to be adjusted as operating conditions of the nebulizer changes. For example, during operation, the resonant frequencies (and the phase offset at off-resonant frequencies) may change. As such, to maintain a constant or near constant phase offset, the frequency of the drive signal may be increased or decreased. This constant or near constant phase offset may be maintained for a period of time, such as while a liquid is being atomized by the nebulizer element.

As liquid is atomized and the bias pressure in the drug reservoir changes, the resonant frequency of the nebulizer element may change. Further, factors besides the bias pressure within the sealed drug reservoir of the nebulizer 260 may change the nebulizer element's resonant frequency. For example, the temperature of the nebulizer element, excess liquid on the nebulizer element, and/or damage to the nebulizer element may cause a variation in the nebulizer element's resonant frequency. However, it may be generally accepted that during operation, changes in the nebulizer element's resonant frequency is generally due to variations in the bias pressure within the drug reservoir of the nebulizer.

The resonant frequency and/or the measured change in resonant frequency may be transmitted to voltage profile 250 by resonant frequency tracker 220. Voltage profile 250 may be used to determine the proper magnitude of voltage to apply to the nebulizer element at a particular resonant frequency to maintain consistent droplet size and dosing of the atomized liquid. In some embodiments, voltage profile 250 may include a table of empirically gathered data. In such embodiments, the resonant frequency may be located in the table, with a corresponding analog or digital signal being output to amplifier 230 that specifies the appropriate magnitude of voltage amplifier 230 should output. For example, a table may include a predetermined voltage magnitude that may be communicated to amplifier 230 when a particular resonant frequency is measured by resonant frequency tracker 220. Voltage profile 250 may also be expressed as a graph of values, with the x-axis being frequency of the waveform generated by resonant frequency tracker 220, and the y-axis representing the appropriate voltage magnitude to be supplied to amplifier 230 such that amplifier 230 outputs an electrical signal of correct magnitude.

A rough description of one set of possible values for voltage profile 250 is that as the resonant frequency of the nebulizer element increases, the desired amplitude of the electrical signal output to the nebulizer will decrease. At a certain threshold, as the resonant frequency continues to increase, the voltage will be held by voltage profile 250 at a minimum level. In some embodiments of voltage profile 250, the signal output to amplifier 230 is determined based on a calculation using the resonant frequency supplied by resonant frequency tracker 220.

The voltage profile may need to be modified or adjusted to accommodate the characteristics (such as surface tension) of different liquids within the drug reservoir of the nebulizer. In some embodiments, a liquid drug, such as Amikacin, is used. In other embodiments, a different liquid drug or liquid (which may be other than a medicine) is used. In some embodiments, the voltage profiles necessary for a number of liquids or liquid drugs may be similar enough that only one voltage profile needs to be used for multiple liquids or liquid drugs. Modifying or replacing voltage profile 250 may involve selecting a different liquid via a user interface on driver 210 or loading different software, firmware, and/or hardware into driver 210.

Resonant frequency tracker 220 may transmit a waveform at or near the nebulizer element's current determined resonant frequency to amplifier 230. Voltage profile 250 may transmit a signal indicating the desired voltage amplitude to be output by amplifier 230 to amplifier 230. This signal from voltage profile 250 may serve to control the gain of the amplifier 230. Based upon the input waveform from resonant frequency tracker 220 and the desired voltage amplitude received from voltage profile 250, amplifier 230 generates an output electrical signal that may be used to drive an aperture plate of the nebulizer. Amplifier 230 may be a variable gain linear power amplifier. In some embodiments, a fixed gain power amplifier may be used in conjunction with a variable gain amplifier or a potentiometer. Further, various other amplifiers or amplifier-based circuits may be used to generate the output electrical signal to drive nebulizer 260.

Current phase shift detector 240 may create a feedback loop to resonant frequency tracker 220. Current phase shift detector 240 may determine the phase shift of the current being output from the amplifier 230. Such a phase shift may be transmitted to resonant frequency tracker 220, thereby allowing resonant frequency tracker 220 to either maintain the same frequency signal (if the phase has not shifted), increase the frequency, or decrease the frequency of the output signal in response to the resonant frequency of the nebulizer element changing as the bias pressure within the sealed drug reservoir changes. Feedback through current phase shift detector 240 may allow driver 210 to periodically or continually adjust the magnitude and frequency of the electrical signal output to the nebulizer element while liquid is being atomized. This may allow for any change in the bias pressure in the liquid reservoir to be continually adjusted for by the driver.

It should be understood that various components of nebulizer system 200 may be implemented using one or more processors and/or non-transitory computer-readable storage mediums. Referring to FIG. 2, various illustrated components may be performed by a single processor or multiple processors. For example, voltage profile 250 may be stored on a computer-readable storage medium and may be accessed by a processor to determine a gain that is provided to amplifier 230.

A driver, such as driver 210 of FIG. 2, may drive a nebulizer element according to a method, such as method 300 of FIG. 3. Alternatively, method 300 may be performed using some other driver of a nebulizer. Method 300 may be performed using various different nebulizers, such as the nebulizers of FIGS. 1A-1D, and FIG. 2. Method 300 may be used to adjust the frequency and/or magnitude of the drive signal used to energize a nebulizer element and/or determine a lock-in frequency. At step 310, the driver may drive an element (also referred to as an aperture plate) of a nebulizer with an electrical signal (also referred to as a drive signal). This electrical signal may be a waveform being generated at a particular frequency and magnitude.

At step 320, the phase shift between the voltage of the electrical signal output to the nebulizer and the current of the electrical signal may be measured. Using this phase shift, at step 330, the lock-in frequency of the nebulizer element may be determined. The frequency of the drive signal may need to be adjusted to determine the lock-in frequency. The lock-in frequency may be the frequency at which a target phase offset occurs. The lock-in frequency may be the frequency at which the nebulizer element was driven to obtain the desired phase offset between the current and voltage of the drive signal. Obtaining the lock-in frequency is further described in relation to FIG. 4. As previously noted, the frequency at which the target phase offset occurs may shift over time as the negative bias pressure within the liquid reservoir of the nebulizer changes and/or other operating conditions of the nebulizer element changes.

At step 340, from the frequency determined at step 320, the bias pressure within the liquid reservoir may be determined at step 340. In some embodiments, a value for the negative bias pressure is not determined. In some embodiments, a frequency difference value between the current frequency used to drive the nebulizer element and a previously determined lock-in frequency is determined. As such, the frequency difference value calculated at step 340 may indicate the amount of frequency drift that has occurred to remain at the desired current-to-voltage phase offset.

At step 350, the magnitude of the voltage of the electrical signal used to drive the nebulizer element may be determined. The magnitude may be determined using the resonant frequency determined at step 330 and/or the negative bias pressure determined at step 340. The frequency difference value that indicates the difference between the lock-in frequency and the current frequency being used to energize the nebulizer element may be used to determine the voltage magnitude. The resonant frequency, the determined frequency difference value, and/or the determined negative bias pressure may be used to consult a table of values of a voltage profile. This table of values may specify the appropriate magnitude of voltage to be used for the electrical signal driving the nebulizer element. Alternatively, the resonant frequency, the determined frequency difference value, and/ or the determined negative bias pressure may be used to calculate the appropriate voltage magnitude to drive the nebulizer element. The appropriate magnitude may correspond to a magnitude intended to maintain a constant dosage rate and droplet size of the liquid being dispensed from the nebulizer. The calculations or table may vary depending on the properties of the liquid being dispensed. As such, a different calculation or table may be used depending on the liquid or characteristics of the liquid being atomized by the nebulizer element.

At step 360, the electrical waveform signal driving the nebulizer element may be adjusted according to the frequency determined at step 330 and/or the magnitude determined at step 350. The operating frequency of the drive signal may be adjusted (e.g., increased or decreased) to maintain the desired current-to-voltage phase offset at step 350. If the resonant frequency of the nebulizer element has not changed (and/or the frequency at which the desired current-to-voltage phase offset has not changed), the frequency and/or the magnitude of the electrical drive signal driving the nebulizer element may not change. Method 300 may repeat while the nebulizer element is being driven by the driver.

Figure 4:
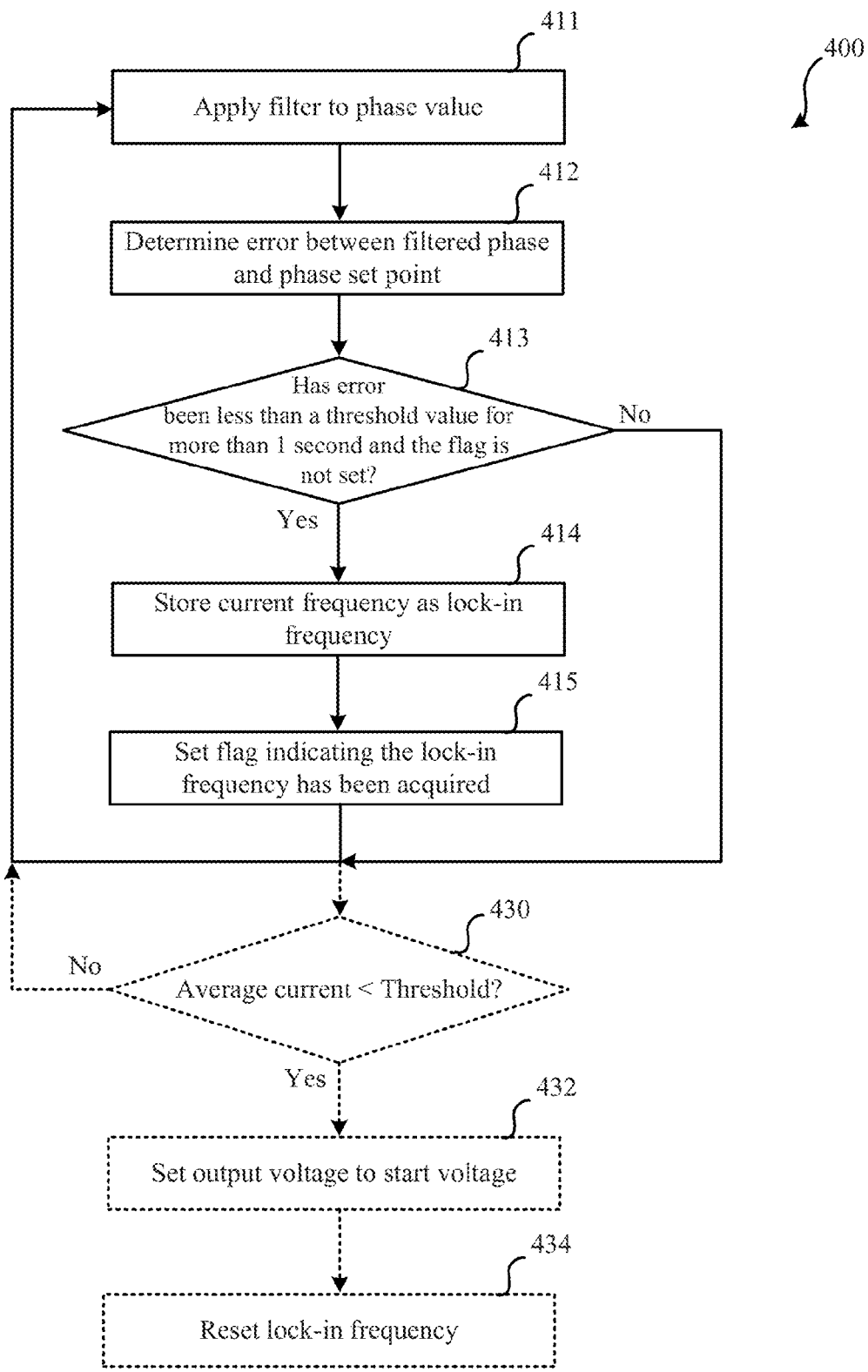
FIG. 4 illustrates a method of initially determining a resonant frequency of a nebulizer element.

A resonant frequency tracker, such as resonant frequency tracker 220 of FIG. 2, may be used in various methods to determine and maintain a drive signal at or near the resonant frequency of a nebulizer element, such as an element of nebulizer 260 of FIG. 2. Another form of frequency generator may be used to generate a frequency for the drive signal to maintain a current-to-voltage phase offset. For example, driver 610 of FIG. 6 may be used. FIG. 4 illustrates an embodiment of a method 400 for determining a resonant frequency of the nebulizer element and adjusting the output electrical signal driving the nebulizer element based on the phase shift between the drive signals' voltage and current. Method 400 of FIG. 4 may be implemented using resonant frequency tracker 220 of FIG. 2, or may be implemented using some other resonant frequency tracker, be it implemented in software, firmware, and/or hardware. It should be understood that method 400 may be applied to maintaining a resonant frequency (corresponding to no current-to-phase offset) or an off-resonance operating frequency (that corresponds to a particular current-to-phase offset), such that a selected phase offset is maintained between the current and voltage of the drive signal. A "lock-in frequency" refers to a frequency of the drive signal at which the desired current-to-voltage phase offset is initially detected. For a resonant frequency, this current-to-voltage phase offset may be zero, for operating off of resonance, the current-to-voltage phase offset may be non-zero, such as thirty degrees.

If the resonant frequency or frequency with the desired current-to-voltage phase offset has not been determined or "locked on" to by a resonant frequency tracker, method 400 may be conducted. The resonant frequency tracker may not have locked on to the resonant frequency or the frequency with the desired current-to-voltage phase offset if, for example, the driver has just been turned on or activated, a new nebulizer is attached to the driver unit, the nebulizer element has been interfered with, or the nebulizer element has been damaged.

At step 411, the resonant frequency tracker may apply an infinite impulse response filter ("IIR filter") to the phase signal received from the current phase shift detector. The IIR filter may be implemented using analog and/or digital components. From this, a filtered phase value may be obtained. This filtered phase value may indicate the current-to-voltage phase offset. The value may be an absolute value (thus not having a positive or negative sign attached to the value). In some embodiments, the components necessary to determine a magnitude of the filtered phase value may tend to be more accurate in determining the magnitude than components that determine a signed value.

Using the filter phase value, the phase error between the filtered phase and desired phase set point (which may be zero for a resonant frequency or non-zero for off-resonance operation) may be determined at step 412. The determined phase error value may be used to determine if the error has been a smaller value than a predefined threshold for greater than a predefined period of time, such as one second, at step 413. In some embodiments, a different length of time is used, such as two seconds or a half second. Further, at step 413 it may be determined whether or not the lock-in flag has been set.

If the error has been less than the threshold value for more than the predefined period of time and the lock-in flag has not yet been set, the current frequency of the signal output to the nebulizer is stored at step 414 as the lock-in frequency. Further, the lock-in flag may be set to indicate that the lock-in frequency has been obtained at step 415. Returning to step 413, if the error has not been less than the threshold value for more than the predefined period of time, method 400 may proceed to step 411. While method 400 is being performed, another method, such as method 800 or method 900, may be being performed that adjusts the frequency of the drive signal. As such, when method 400 is repeated, the result may vary due to changes in operating characteristics of the nebulizer and changes in the frequency of the drive signal.

In some embodiments, additional steps may be performed to determine if the current has passed a threshold. For example, if the current becomes lower than a predefined current threshold, it may be advantageous to restart a sweep to locate the lock-in frequency. At step 430, if the average current of the drive signal is less than some threshold current value, the output voltage frequency and/or voltage magnitude of the drive signal may be set to a start voltage frequency and voltage magnitude at step 432. At step 434, the lock-in frequency determined by the resonant frequency tracker may be reset to an initial value and the lock-in flag may be cleared. If the average current is not less than a threshold current value, steps 432 and 434 may not be performed in some embodiments.

Figure 3:
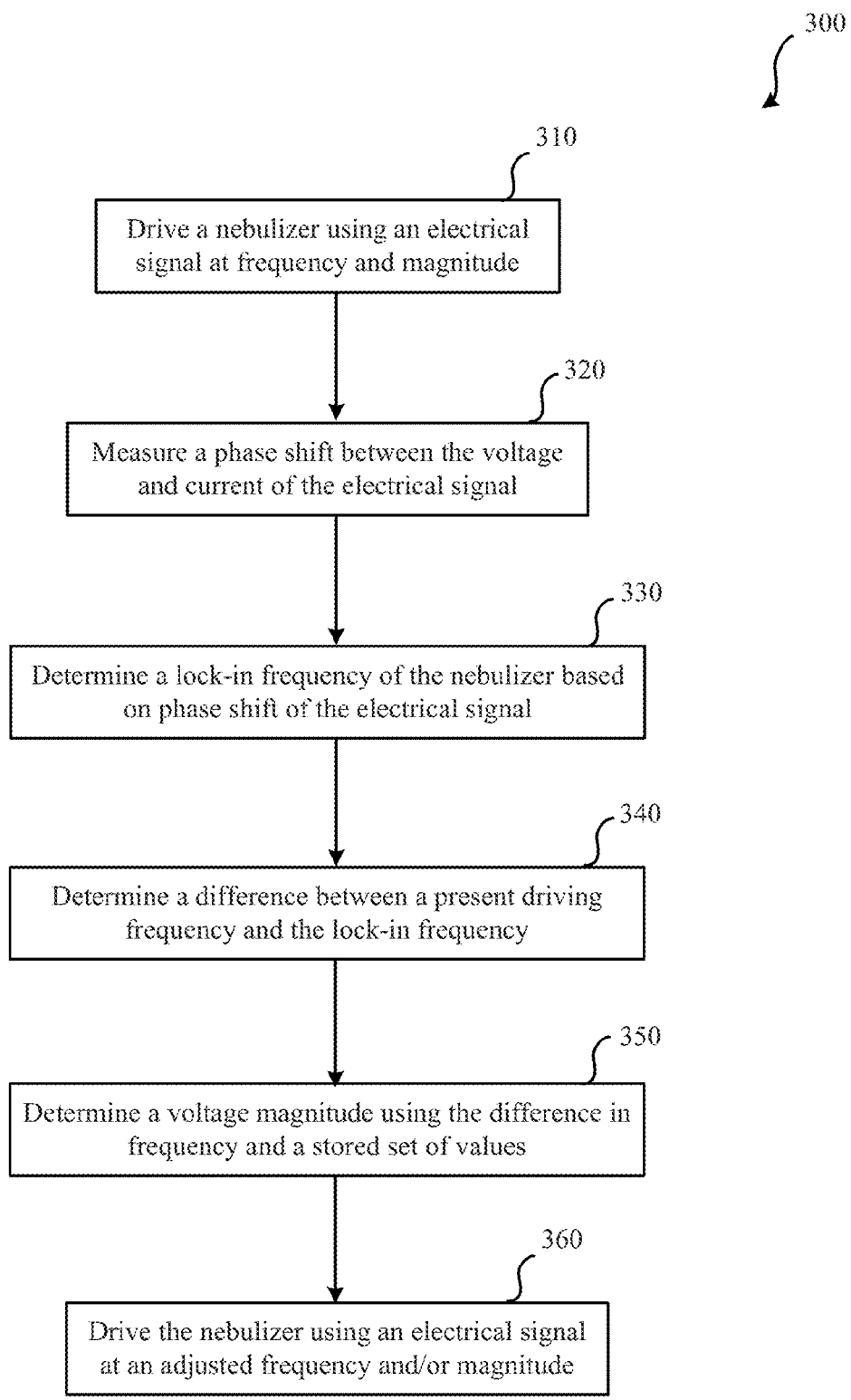
FIG. 3 illustrates a method of driving a nebulizer with a driver.
Figure 5:
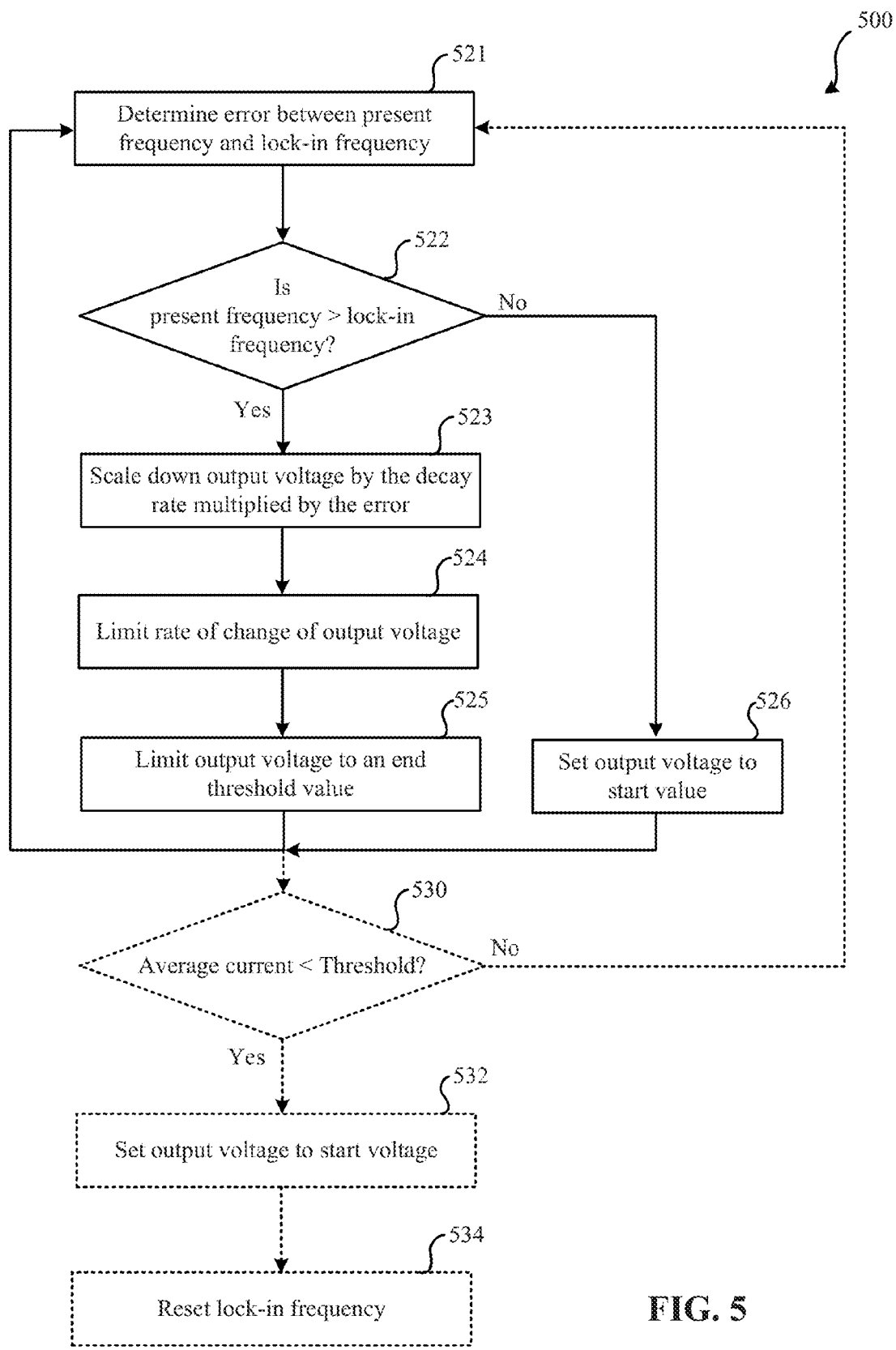
FIG. 5 illustrates a simplified method of adjusting the frequency output by a driver using a resonant frequency tracker to maintain the nebulizer element vibrating at its current resonant frequency.

Once the lock-in frequency has been determined, which may involve lock-in flag of step 414 being set, another method may be performed. FIG. 5 illustrates a method 500 for adjusting the voltage magnitude of the drive signal. Method 500 may be performed while maintaining the nebulizer element vibrating at a frequency having the desired current-to-voltage phase offset (which may be zero or non-zero). Method 500 may represent a more detailed embodiment of step 350 of FIG. 3. An error rate value that indicates the amount of error between the present frequency of the drive signal and lock-in frequency may be determined at step 521.

A determination of whether the present frequency of the drive signal being generated by the resonant frequency tracker is greater than the lock-in frequency of the nebulizer element may be made at step 522. If yes, at step 523, the output voltage may be scaled by a decay rate multiplied by the error rate value determined at step 521. The rate of change of the voltage of the drive signal may be limited such that the voltage is not changed at a rate above and/or below a threshold rate at step 524. The output voltage may be limited to the end voltage at step 525. This may prevent the output voltage from exceeding maximum and/or minimum threshold values. Next, method 500 may proceed to step 530. If the present frequency is determined to not be greater than the resonant frequency at step 522, the output voltage of the drive signal may be set to a start voltage at step 526, and method 500 may proceed to step 530.

Following steps 525 and 526, method 500 may repeat in order to control the magnitude of voltage output to the nebulizer element. In some embodiments, method 500 may proceed to step 530. At step 530, it may be determined if the current of the drive signal is less than a threshold current value. If so, the output voltage magnitude and frequency may be set to the start voltage at step 532 and the lock-in frequency may be reset at step 534.

In some embodiments, as discussed, rather than attempting to vibrate a nebulizer element directly on a resonant frequency, it may be possible to more accurately control an amount of liquid aerosolized if a nebulizer is operated off-resonance. Operation with a zero degree phase shift between the voltage and current of the drive signal transmitted to the nebulizer element may be indicative of the nebulizer element being vibrated at a resonant frequency. Rather than attempting to operate at a zero degree phase between the current and voltage output by a nebulizer driver, a phase offset, such as 30 degrees, may be maintained. Such a phase shift off of a resonant frequency of the nebulizer element may result in a more accurate dosage of an atomized medicine being delivered to a patient. For example, if the resonant frequency of the nebulizer element changes and some amount of phase offset drift occurs, the amount of liquid aerosolized may not vary significantly of the nebulizer element is being energized at a non-resonant frequency. However, at and/or around zero degrees phase shift between the current and voltage of the drive signal, phase shift drift may result in a significant variance in the amount of liquid aerosolized as the nebulizer elements shifts from being energized at a resonant frequency to a non-resonant frequency.

Figure 6:
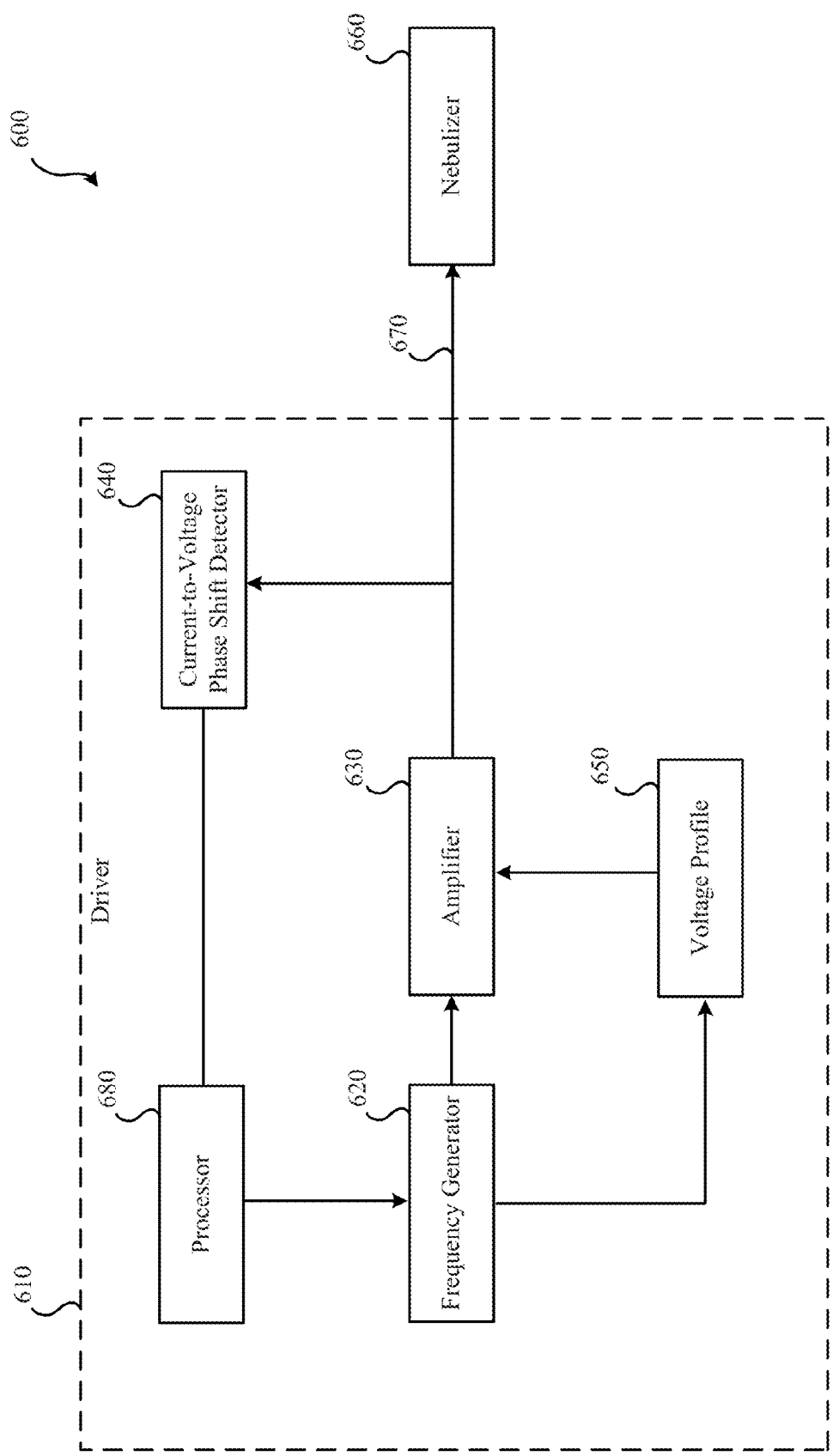
FIG. 6 illustrates another embodiment of a driver coupled with a nebulizer.

While some embodiments of a nebulizer may use a reservoir having a negatively-biased pressure, other embodiments of nebulizers may use a reservoir to store liquid that is not negatively-biased. Embodiments of FIGS. 6-9 may be used with or without a negatively-biased liquid reservoir. FIG. 6 illustrates a simplified block diagram of a nebulizer system 600. Nebulizer system 600 may represent a more detailed embodiment of nebulizer system 200. As such, previously detailed methods and systems may involve use of nebulizer system 600. Some components of nebulizer system 600 may represent the same components as nebulizer system 200. It should be understood that functions of at least some of the components of nebulizer system 200 and nebulizer system 600 may be performed by processor 680 or some other processor. As such, nebulizer system 600 may include one or more processors. Nebulizer system 600 may also contain a non-transitory computer-readable storage medium.

Nebulizer 660 may represent nebulizer 100-*a* of FIG. 1A or may represent some other nebulizer such as those in the referenced applications and/or in FIGS. 1B-1D. Nebulizer 660 may be connected to driver 610 via a cable 670. Driver 610 may represent driver 152 of FIG. 1B or may be some other driver. Cable 670 may allow driver 610 to transmit an electrical waveform signal of varying frequency and magnitude (of voltage) through cable 670 to drive an element of nebulizer 660.

Driver 610 may include amplifier 630, a current-to-voltage phase shift detector 640, frequency generator 620, voltage profile 650, and processor 680. Based upon the phase shift between the current output to nebulizer 660 and the voltage output, the nebulizer element's resonant frequency may be determined. It may be assumed that the resonant frequency occurs when there is a zero degree phase difference between the current and voltage outputs by amplifier 630.

The determination of the phase difference between the output voltage and output current may be performed by current-to-voltage phase shift detector 640. Current-to-voltage phase shift detector 640 may monitor the phase shift between the phase of the current output by amplifier 630 to nebulizer 660 and the phase of the voltage output by amplifier 630 to nebulizer 660. Based upon the phase shift between the voltage and current observed by current-to-voltage phase shift detector 640, a frequency of a waveform output by frequency generator 620 may be changed by processor 680 such that amplifier 630 outputs an electrical waveform signal with the predefined phase shift between the voltage and current of the signal driving the element of nebulizer 660. Processor 680 may monitor the phase shift indicated by current-to-voltage phase shift detector 640 and may provide an output to frequency generator 620 that indicates whether the frequency should be held constant or changed. It should be understood that current-to-voltage phase shift detector 640 and/or frequency generator 620 may be part of processor 680. In some embodiments, the phase shift detector communicates directly with frequency generator 620.

On startup, processor 680 may cause frequency generator 620 to begin generating a first predefined voltage start frequency and magnitude. The first predefined frequency may be selected such that it is expected to be less than the frequency of the desired phase offset for all or most nebulizers. It should be understood that due to variances between nebulizers and drivers, the precise frequency at which a particular phase offset occurs (and the frequencies at which resonant frequencies occur) may vary. The first predefined start frequency may be 122 kHz. Processor 680 may increase the frequency output by frequency generator 620 until the target phase offset is indicated by current-to-voltage phase shift detector 640. If a second predefined frequency is reached without the target phase offset being reached, the processor 680 may start again by sweeping or stepping from the first predefined start frequency. In some embodiments, the second predefined frequency is 145 kHz. As such, it may have been previously determined, such as via experimentation, that the target phase offset occurs for all or almost all nebulizer elements in the range of when the operating frequency of the drive signal is between 122 kHz and 145 kHz. When the target phase offset is reached, processor 680 may cease causing the frequency generated by frequency generator 620 to increase or decrease.

In some embodiments, current-to-voltage phase shift detector 640 may not be configured to identify whether a phase shift is positive or negative. In addition to causing a phase offset between the output voltage and current to be maintained, processor 680 may determine whether various other conditions have been satisfied. Processor 680 may determine whether the impedance of nebulizer 660 is above or below a predefined limit. Also, processor 680 may determine whether the phase shift is increasing or decreasing as the frequency output by frequency generator 620 increases (or decreases). If at a frequency the target phase offset is present, but the impedance of the nebulizer is not below (or above) a threshold and/or the phase offset is increasing as the frequency is increasing (a positive slope), the processor 680 may ignore the frequency and continue searching for another frequency within the range defined by the first and second predefined frequencies where each of the conditions is satisfied. Other embodiments may use a negative slope or a slope threshold for phase offset as a condition required to be satisfied.

In some embodiments, the frequency being generated by frequency generator 620 may be transmitted to voltage profile 650. Voltage profile 650 may be used to determine the proper magnitude of voltage to output to nebulizer 660 at a particular frequency to maintain consistent droplet size and dosing of the atomized liquid. In some embodiments, voltage profile 650 may include a table of empirically gathered data. In such embodiments, frequencies may be indicated in the table, along with magnitude values. An analog or digital signal may be output to amplifier 630 that specifies the magnitude of voltage that amplifier 630 should output. For example, voltage profile 650 may include a predetermined voltage magnitude that may be communicated to amplifier 630 when a particular frequency is generated by frequency generator 620. Voltage profile 650 may also be expressed as a graph of values, with the x-axis being frequency of the waveform generated by frequency generator 620, and the y-axis representing the appropriate voltage magnitude to be supplied to amplifier 630 such that amplifier 630 outputs an electrical signal of correct magnitude. Voltage profile 650 may be implemented as part of processor 680.

The voltage profile may need to be modified or adjusted to accommodate the characteristics (such as surface tension) of different liquids within the drug reservoir of the nebulizer. In some embodiments, a liquid drug, such as Amikacin, is used. In other embodiments, a different liquid drug or liquid is used. In some embodiments, the voltage profiles for a number of liquids or liquid drugs may be similar enough that only one voltage profile needs to be used for multiple liquids or liquid drugs. Modifying or replacing voltage profile 650 may involve selecting a different liquid via a user interface on driver 610 or loading different software, firmware, and/or hardware into driver 610.

Based upon the input waveform from frequency generator 620 and the desired voltage amplitude received from voltage profile 650, amplifier 630 may generate an output drive signal that may be used to drive a nebulizer element, such as an aperture plate. Amplifier 630 may be a variable gain linear power amplifier. In some embodiments, a fixed gain power amplifier may be used in conjunction with a variable gain amplifier or a potentiometer. Further, various other amplifiers or amplifier based circuits may be used to generate the output electrical signal to drive nebulizer 660.

Current-to-voltage phase shift detector 640 may create a feedback loop to frequency generator 620 via processor 680. Current-to-voltage phase shift detector 640 may determine the phase shift of the current to voltage being output from the amplifier 630. Such a phase shift may be used to adjust the frequency output by frequency generator 620, thereby allowing frequency generator 620 to either maintain the same frequency signal (e.g., to maintain a particular phase offset), increase the frequency, or decrease the frequency of the output signal (e.g., to adjust the phase offset). Feedback through phase shift detector 640 may allow driver 610 to periodically or continually adjust the magnitude and frequency of the drive signal output to the nebulizer element while liquid is being atomized. For example, if there is a change in bias pressure within a liquid reservoir (e.g., due to liquid evacuating the reservoir) feeding liquid to nebulizer 660, the frequency at which a particular phase offset occurs may drift. This drift may be adjusted for by driver 610.

Figure 7:
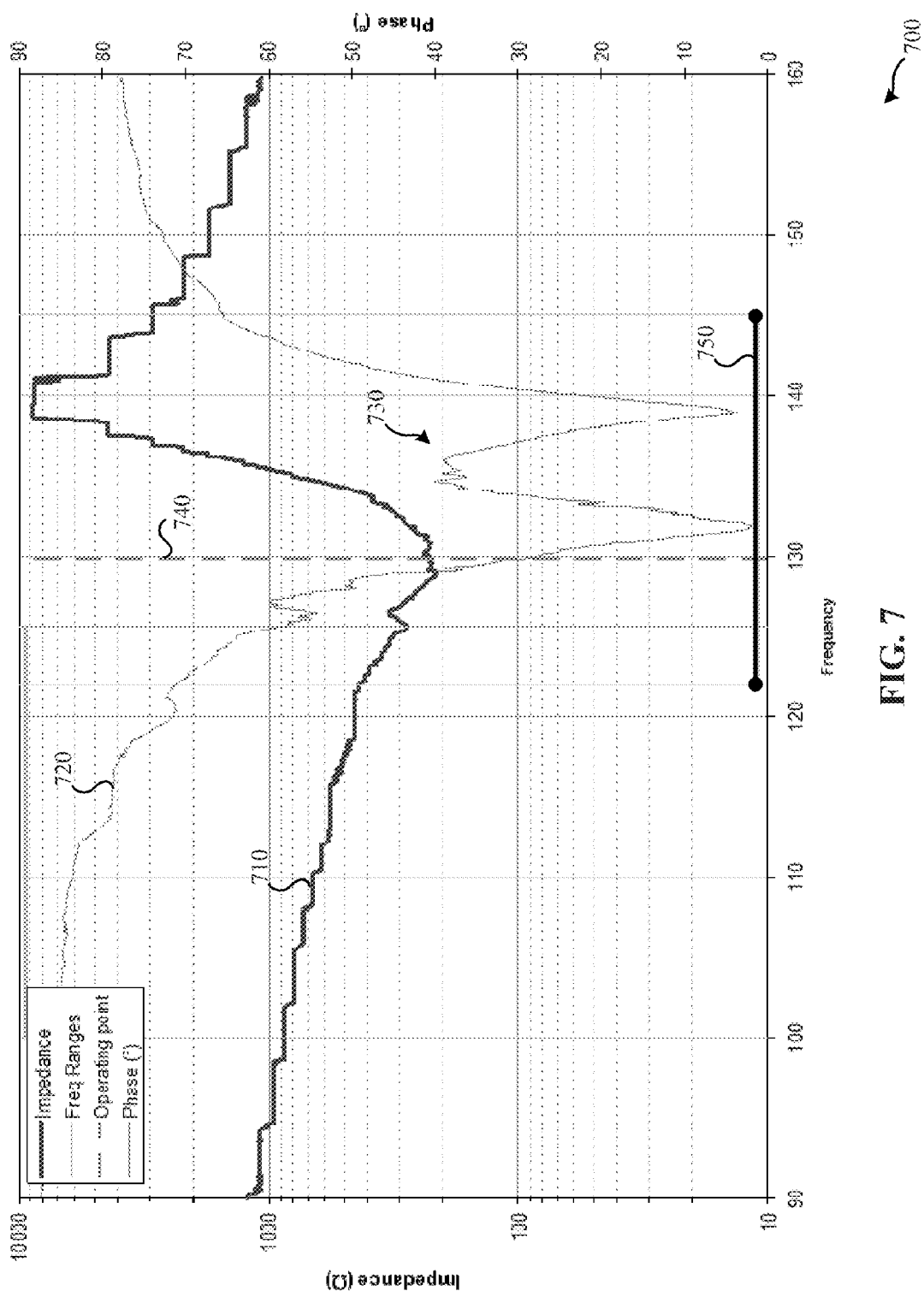
FIG. 7 illustrates an embodiment of a graph illustrating phase offset and impedance of a nebulizer element when excited by a drive signal at different voltage frequencies.

FIG. 7 illustrates an embodiment of a graph 700 showing phase offset between drive signal voltage and drive signal current and impedance of a nebulizer element at different voltage frequencies. Impedance 710 indicates the impedance of a nebulizer element at various voltage frequencies. Impedance 710 may be determined by measuring the current and voltage applied to a nebulizer element, then using the measured values to calculate the impedance. Phase offset 720 indicates phase offset between the voltage of the drive signal and the current of the drive signal. This drive signal is used to excite the nebulizer element and cause it to vibrate and atomize a liquid. The phase offset indicated by phase offset 720 may be measured by a phase shift detector, such as phase shift detector 640 of FIG. 6.

Graph 700 illustrates the phase and impedance of a particular nebulizer element at various voltage frequencies. It should be understood that other nebulizer elements, including those which were attempted to be manufactured to the same specifications as the nebulizer element used to produce graph 700, may result in varying impedance and/or phase offset values. As such, at a particular frequency, different nebulizer elements may exhibit different characteristics.

For the nebulizer element used to produce graph 700, it may be desirable for the nebulizer element to be energized off a resonant frequency. While energizing on a resonant frequency may result in a greater amount of liquid being atomized, it may be difficult to continually excite the nebulizer element at the resonant frequency. One reason for this may be that the resonant frequency of the nebulizer element may change as liquid is dispensed from a reservoir of the nebulizer. By energizing the nebulizer element off a resonant frequency, the amount of liquid atomized may be more easily regulated and maintained constant. Such consistency may be particularly important when the liquid being nebulized is a medicine.

For the nebulizer element used to produce graph 700, it was previously determined via testing the nebulizer element would be energized such that a 30° phase offset is maintained between the applied voltage and current of the drive signal. Further, while characteristics may vary from nebulizer element to nebulizer element, nebulizer elements that are manufactured according to a common specification may be expected to have characteristics similar enough such that the frequency at which the desired phase delta occurs can be predicted to within a frequency range. This frequency range is indicated by frequency range 750. Frequency range 750 indicates a low-frequency and a high-frequency. Within frequency range 750, a frequency at which the target phase offset of 30° occurs may be attempted to be located. In other embodiments, a voltage-to-current phase offset of between 0 degrees and 60 degrees is used. In some embodiments, a voltage-to-current phase offset of between 10 degrees and 70 degrees is used.

In some embodiments, scanning for the frequency at which the target phase offset occurs may begin at the low-frequency of frequency range 750. In the illustrated embodiment of graph 700, this low-frequency is 122 kHz. At 122 kHz, the phase offset of the nebulizer element is approximately 72°. Since this is not the 30° target phase offset that was predetermined, frequency scanning may occur. The frequency of voltage applied to the nebulizer element may be increased, either continuously or by stepping. For example, steps of 250 Hz may be used. After each step, the phase offset between the current and voltage of the drive signal may be determined. At 130 kHz, the target phase offset may be realized in the illustrated embodiment of graph

700. Operating point 740 indicates this frequency. Once this operating frequency has been reached, the frequency of the voltage of the drive signal may no longer be changed. Rather, the frequency may be maintained at the operating point 740.

In graph 700, the first frequency at which a 30° phase offset exists is the frequency to be used as operating point 740. However, within frequency range 750, it can be seen that multiple other frequencies have a phase offset of 30°. In graph 700, approximately 134 kHz, 137 kHz, and 141 kHz also have a phase delta of 30°. If scanning the frequency range 750 started down from the high frequency of frequency range 750 or the 30° phase offset at 130 kHz was initially missed due to a scanning error, one of these other instances of the 30° phase offset may first be located. These other instances of a 30° phase offset may be less desirable due to atomization characteristics at those frequencies.

In addition to examining the phase offset, other characteristics of the drive signal transmitted to the nebulizer element may be used in order to determine if the desired operating point having the target phase offset has been reached. Other characteristics may include the impedance of the nebulizer element and the slope of the phase offset. Referring to impedance, a maximum and/or minimum impedance threshold may be defined such that if the target phase offset is realized but the nebulizer element impedance does not meet the maximum and/or minimum impedance threshold, scanning of frequency range 750 continues in an attempt to locate another frequency where the target phase offset occurs. Referring to 141 kHz, a 30° phase offset exists; however impedance is approximately 9000 ohms. Similarly, referring to 137 kHz, a 30° phase offset exists; however impedance is approximately 3000 ohms. A maximum impedance threshold of, for example, 400 ohms would be exceeded in either instance. Thus, 141 kHz and 137 kHz would not be used as the operating point due to violation of a maximum impedance threshold of 400 ohms.

Phase offset region 730, between approximately 133 kHz and 138 kHz, shows a local maximum in phase offset. It should be understood that the components used to determine phase offset may only measure magnitude and not sign (positive or negative), as such phase offset region 730 may correspond to phase offset that is negative. Accordingly, phase offset 720 indicates a phase delta magnitude.

In addition to impedance thresholds, slope may be used to exclude particular phase offsets matching the target phase offset within frequency range 750. Based on empirical evidence, it may be known that, at the desired operating point, the phase delta will be increasing or decreasing as the voltage frequency of the drive signal is increased or decreased. For the nebulizer element of graph 700, it may be known that, as frequency is increased, the magnitude of phase offset will be decreasing at the desired operating point (i.e., phase offset 720 has a negative slope). As such, 134 kHz may be eliminated as a candidate for being the desired operating point. While 134 kHz may match the target phase offset and may meet impedance thresholds, as frequency is increasing so is the phase delta (i.e., the phase offset has a positive slope).

In the embodiment of graph 700, only a single frequency within frequency range 750 satisfies the phase offset requirement, the maximum impedance threshold, and the phase offset slope requirement. As such, only frequency 130 kHz is eligible to be used as operating point 740. If, while scanning up through frequency range 750, 130 kHz is missed (e.g., due to a scanning error), the high frequency of frequency range 750 may be reached (145 kHz). At this point, scanning of frequencies may begin again from the low frequency of frequency range 750.

Figure 8:
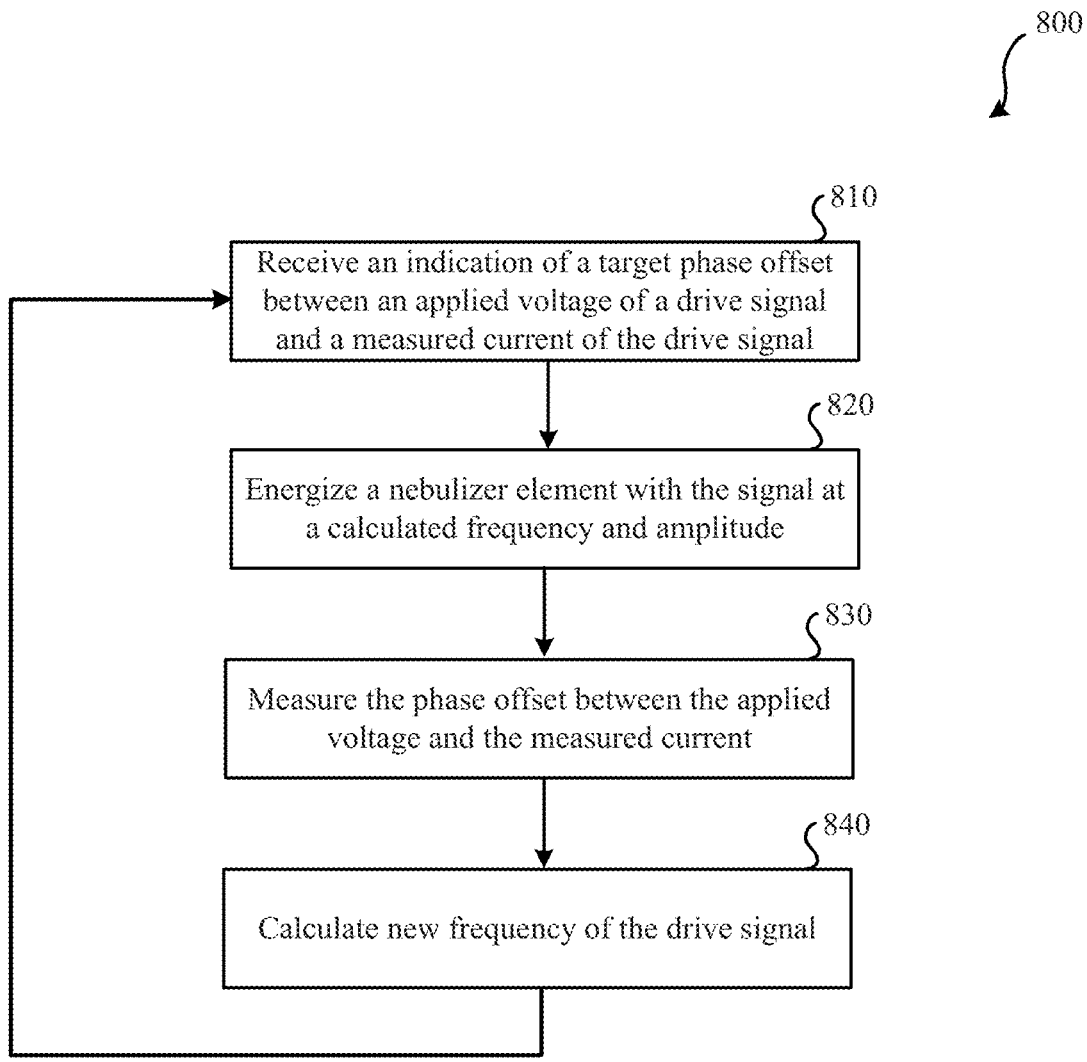
FIG. 8 illustrates an embodiment of a method for maintaining a phase offset of a nebulizer drive signal.

Various methods may be performed that maintain a phase offset between the current and voltage of a drive signal used to excite a nebulizer element. FIG. 8 illustrates an embodiment of method 800 for locating and maintaining a phase offset of a nebulizer drive signal. Method 800 may be used to maintain various phase offsets between a current and voltage of a nebulizer element. For example, it may be possible to use method 800 to maintain any non-zero phase offset between the current and voltage of the nebulizer drive signal. In some embodiments, a target phase offset of 30 degrees is desired between the current and voltage of the drive signal. The phase offset may be selected based on a previously identified set-point that produces desirable atomization characteristics by the nebulizer element (e.g., a high flow rate, little variation in flow rate if some frequency drift or phase offset drift occurs).

Method 800 may be performed with a nebulizer and a nebulizer driver. For example, nebulizer system 600 of FIG. 6 may be used to perform method 800. Nebulizers such as those illustrated in FIGS. 1A-1D may be used in performing method 800. Means for performing method 800 include the nebulizers and nebulizer drivers previously described.

At step 810, an indication of a target phase offset may be received. This target phase offset may be programmed into or otherwise stored by the nebulizer drive. For example, phase shift detector 640 or processor 680 of FIG. 6 may store an indication of the target phase offset that is desired to be maintained between the current and voltage of the drive signal applied to the nebulizer element. In some embodiments, the target phase offset is non-zero. For example, the target phase offset is 30°. A zero phase offset may be associated with the nebulizer element operating at a resonant frequency. The indication of the target phase offset may be received by the nebulizer driver at the time of manufacture or while being programmed or reprogrammed following manufacture. Additionally, at step 810, a frequency range which indicates a minimum frequency and a maximum frequency may be received by the nebulizer system performing method 800. Within this frequency range, the driver may be permitted to vary the frequency of the drive signal to obtain the target phase offset.

At step 820, the nebulizer element may be energized with the drive signal at a calculated frequency and calculated magnitude. During a first iteration of method 800, an initial predefined frequency and a predefined amplitude may be used for the drive signal. From the predefined frequency and predefined magnitude or the calculated frequency and calculated magnitude, the nebulizer driver may increase or decrease the frequency of the drive signal until the target phase offset is obtained. In the detailed embodiment of method 800, the frequency of the drive signal may be increased from the initial predefined frequency until the desired phase offset is obtained. It should be understood that in other embodiments the frequency may be decreased from the initial predefined frequency. As example, referring to graph 700 of FIG. 7, the initial predefined frequency may be 122 kHz. Accordingly, the initial predefined frequency used for graph 700 is also the minimum frequency of the frequency range across which the drivers are permitted to vary the frequency of the drive signal to obtain the target phase offset.

At step 830, the phase offset between the voltage and the current of the drive signal used to energize the nebulizer element may be measured. Referring to nebulizer system 600 of FIG. 6, phase shift detector 640 may measure the phase difference between the voltage and current of the drive signal provided to an element of nebulizer 660.

The frequency of the drive signal that is to be applied to the nebulizer element may be calculated at step 840. This may involve increasing the frequency of the drive signal by a set amount. As such, the frequency of the drive signal may be increased in steps. In other embodiments of method 800, the frequency of the drive signal may be continuously increased until the target phase offset is reached. If a maximum frequency of the frequency range across which the driver is permitted to use to excite the nebulizer element is reached, the frequency of the drive signal may be decreased to the minimum frequency of frequency range. As an example of this, referring to graph 700, the frequency of the drive signal may be increased to 145 kHz. Once 145 kHz is reached, the frequency of the drive signal may be reset to 122 kHz. While the illustrated embodiment of method 800 involves increasing the frequency of the drive signal across the frequency range, other embodiments may involve decreasing frequency of the drive signal across the frequency range. Method 800 may repeat during operation of a nebulizer system to maintain a particular phase offset. As such, during operation, method 800 may beused to increase or decrease the frequency of the drive signal as necessary to maintain a predefined phase offset. In some embodiments, until a lock-in frequency is obtained, frequency may only be adjusted in one direction (e.g., increased). Once the lock-in frequency has been obtained, frequency of the drive signal may be increased and/or decreased to maintain the predefined phase offset.

Figure 9:
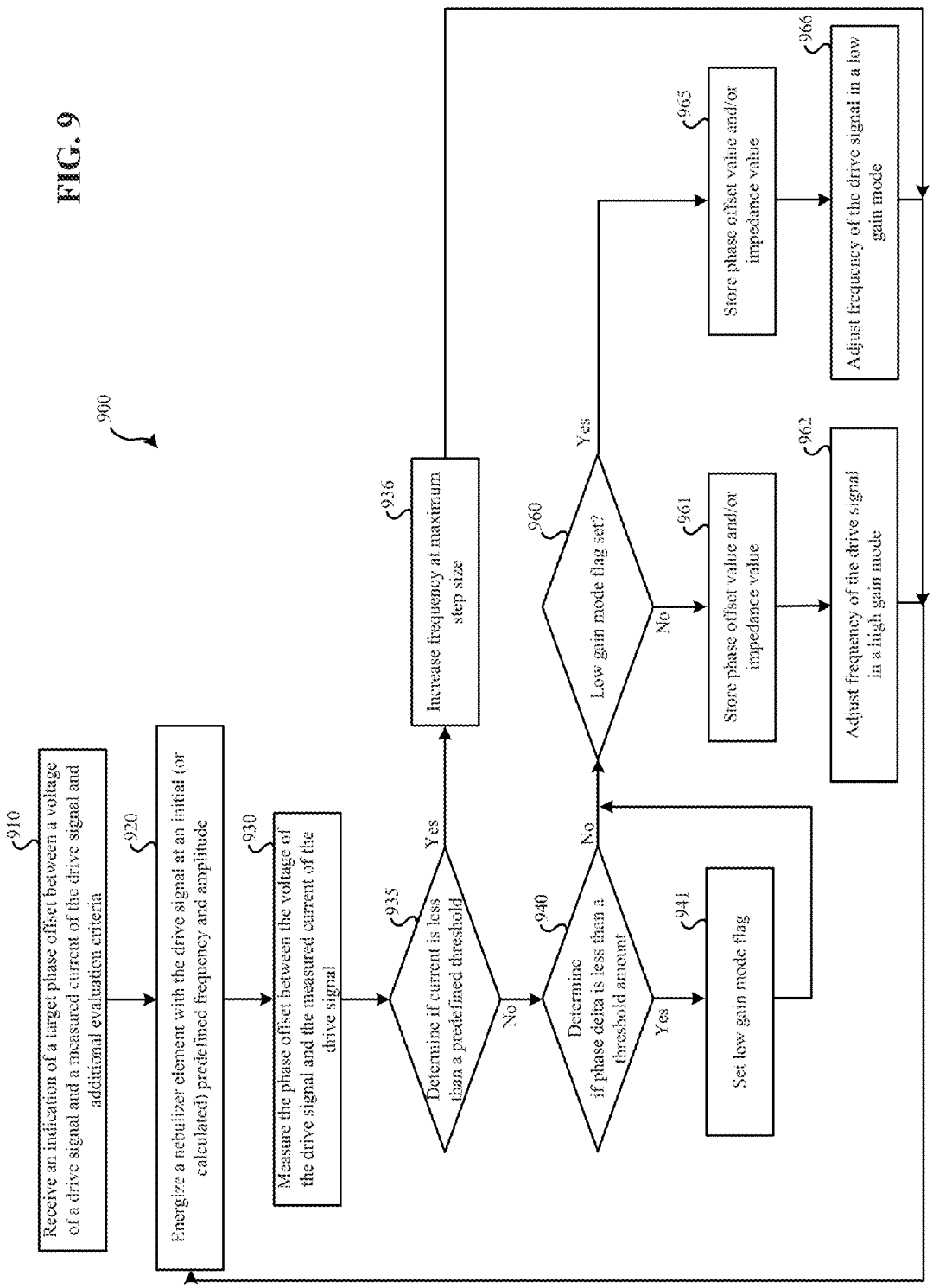
FIG. 9 illustrates an embodiment of a method for setting and maintaining a phase offset of a nebulizer drive signal.

FIG. 9 illustrates an embodiment of method 900 for maintaining a phase offset of a nebulizer drive signal. Method 900 may represent a more detailed embodiment of method 800 of FIG. 8. Method 900 may be used to maintain various phase offsets between a current and voltage of a drive signal used to energize a nebulizer element. For example, it may be possible to use method 900 to maintain various non-zero phase offsets between the current and voltage of the nebulizer drive signal. In some embodiments, a phase offset of 30° is desired between the current and voltage of the drive signal. The phase offset may be selected based on a previously identified phase offset that produces desirable atomization characteristics by the nebulizer element (e.g., a high flow rate, little variation in flow rate if some frequency drift or phase offset drift occurs). Method 900 may be performed with a nebulizer and a nebulizer driver. For example, nebulizer system 600 of FIG. 6 may be used to perform method 900. Nebulizers such as those illustrated in FIGS. 1A-1D may be used in performing method 900. Means for performing method 900 include the nebulizers and nebulizer drivers previously described.

At step 910, an indication of a target phase offset may be received. This target phase offset may be programmed into or otherwise stored by the nebulizer drive unit. For example, phase shift detector 640 or processor 680 of FIG. 6 may store an indication of the target phase offset that is desired to be maintained between the current and voltage of the drive signal applied to the nebulizer element. In many embodiments, the target phase offset is non-zero. For example, the target phase offset could be 30°. A zero phase offset may be associated with the nebulizer element operating at one of its resonant frequencies. The indication of the target phase offset may be received by the nebulizer driver at the time of manufacture or while being programmed or reprogrammed following manufacture. Additionally, at step 910, a frequency range which indicates a minimum frequency and a maximum frequency may be received. Within this frequency range, the driver may be permitted to vary the frequency of the drive signal to obtain the target phase offset.

Further, at step 910 one or more additional evaluation criteria may be received and stored by the driver for use in determining whether a frequency should be locked onto once the target phase offset has been determined. Within the frequency range within which the driver is permitted to vary the frequency of the drive signal, multiple frequencies may exist at which the phase offset between the current and voltage of the drive signal is equal to the target phase offset. However, only one of these phase offset points which match the target phase offset may be desired for use as the operating point. For example, referring to graph 700 of FIG. 7, within frequency range 754 points exist where the phase offset is 30°. Additional evaluation criteria which may be used to determine the desired operating point may include minimum and/or maximum impedance thresholds. Additional evaluation criteria may also include a slope (e.g., positive, negative, or threshold-based) of the phase offset and/or the impedance of the nebulizer element.

At step 920, during a first iteration of method 900, the nebulizer element may be energized with the drive signal at an initial predefined frequency and a predefined amplitude. During subsequent iterations of method 900, the nebulizer element may be energized with the drive signal at a calculated frequency and calculated amplitude based on phase offset measurements. From the calculated or predefined frequency, the nebulizer driver may increase or decrease the frequency of the drive signal until the target phase offset is obtained. In the illustrated embodiment of method 900, the frequency of the drive signal is increased from the initial predefined frequency until the lock-in frequency is obtained, then the frequency is increased and/or decreased as necessary to maintain the phase offset. It should be understood that in other embodiments the frequency may be decreased from the initial predefined frequency. As example, referring to graph 700 of FIG. 7, the initial predefined frequency may be 122 kHz. Accordingly, the initial predefined frequency used for graph 700 is also the minimum frequency of the frequency range across which the drivers permitted to vary the frequency of the drive signal to obtain the target phase offset. Referring to nebulizer system 600, frequency generator 620 may create a waveform having a frequency as indicated by processor 680 and/or phase shift detector 640. The magnitude of the drive signal to be output may be defined by voltage profile 650 in accordance with the frequency being generated by frequency generator 620. Amplifier 630 may use the waveform from frequency generator 620 and the indication of amplitude from voltage profile 650 to create the drive signal, which is output to nebulizer 660.

At step 930, the phase offset between the voltage and the current of the drive signal used to energize the nebulizer element may be measured. Referring to nebulizer system 600 of FIG. 6, for example, phase shift detector 640 may measure the phase difference between the voltage and current of the drive signal output to nebulizer 660. Additionally at step 930, the impedance of the nebulizer element may be measured (or calculated). A calculation of the impedance of the nebulizer element may be obtained using the current and voltage of the drive signal according to Ohm's law. Accordingly, the impedance of the nebulizer element may be determined at the nebulizer driver.

At step 935, a determination may be made as to whether the current of the drive signal is below a predefined threshold. If so, the frequency of the drive signal may be increased (or decreased) according to a maximum predefined step size at step 936. Method 900 may then return to step 920.

If the current is above the predefined threshold of step 935, method 900 may proceed to step 940. At step 940, it may be determined if a phase delta is less than a threshold amount. "Phase delta" refers to a difference in magnitude between the target phase offset and the measured phase offset. If it is determined that the phase delta is not within a predefined threshold range of the target phase offset, such as 1°, 2°, 3°, 4°, 5°, 10° (or some other threshold range, method 900 may proceed to step 960. If it is determined that the phase delta is within the predefined threshold range of the target phase offset, a low gain mode flag may be set at step 941, then method 900 may proceed to step 960.

Further, at step 940, the additional evaluation criteria may be evaluated. This may involve determining if a minimum and/or maximum threshold impedance is satisfied. Additionally, the slope of the phase offset and/or the slope of the impedance may be determined. The slope may be determined by comparison of one or more of the previously measured impedance and/or phase offset measurements to the currently measured impedance and/or phase offset measurements. Whether the slope is positive or negative may serve as an evaluation criteria. A slope magnitude may also serve as an evaluation criteria. If the frequency of the drive signal is being increased and the phase offset is also increasing, this may be evidence of a positive slope. For example, referring to graph 700 of FIG. 7, such a positive slope of phase offset is present around 133 kHz. If the frequency of the drive signal is being increased and the phase offset is decreasing, this is evidence of a negative phase offset slope. Again, referring to graph 700, such a negative slope is present in the vicinity of 130 kHz. Regardless of whether the phase delta is less than the threshold value, if the additional evaluation criteria at step 940 are not satisfied, method 900 may proceed to step 960. At step 960, the impedance and/or phase offset value measured may be stored. These stored values may later be used for determination of the slope of the nebulizer element's impedance and/or the slope of the phase offset.

If at step 960 it is determined that the low gain mode flag has not been set, method 900 may proceed to step 961. At step 961, the current phase offset value and/or the impedance of the nebulizer element (based on the voltage and current of the drive signal) may be stored, such as for a slope calculation of impedance or phase offset. The adjustment of frequency at step 962 may occur as part of a "high gain" mode. Because at step 940 it was determined that the target phase offset was not within a predefined threshold, it may be expected that a significant change in frequency will need to occur before the target phase offset is realized. Adjustment of the frequency at step 962 in the high gain mode may permit for faster scanning/stepping of frequencies. In some embodiments, high gain mode may involve a larger frequency step size being used for adjustment than a "low gain" mode. As such, at step 962, the frequency may be increased by a large step, such as 250 Hz. Following step 962, the newly calculated frequency (and possibly amplitude) for the drive signal may be used to energize the nebulizer element at step 920 and the phase offset (and the impedance) of the nebulizer element may again be measured at step 930.

At step 962, if a maximum frequency of the frequency range across which the driver is permitted to use to excite the nebulizer element is reached, the frequency of the drive signal may be set to the minimum frequency of frequency range. As an example of this, referring to graph 700, the frequency of the drive signal may be increased to 145 kHz. Once 145 kHz is reached, the frequency of the drive signal may be reset to 122 kHz. While the illustrated embodiment of method 900 involves increasing the frequency of the drive signal across the frequency range, other embodiments may involve decreasing frequency of the drive signal across the frequency range.

Returning to step 940, if it is determined the phase delta is less than a threshold amount and the low gain mode flag was set at step 941, method 900 may proceed to step 965 following step 960. At step 965 the phase offset value and/or the impedance of the nebulizer element may be stored. These stored values may be used for determination of the slope of the nebulizer elements impedance and/or the slope of the phase offset. If the phase delta is zero, this means that the measured phase offset at step 930 is equal to the target phase offset.

The adjustment of frequency at step 966 may occur as part of a "low gain" mode. Because at step 940 it was determined that the target phase offset was within a threshold range of the target phase offset, it may be expected that only a small change in frequency will need to occur before the target phase offset is realized. Adjustment of the frequency at step 966 in the low gain mode may permit for more precise scanning/stepping of frequencies. In some embodiments, low gain mode may involve a smaller frequency step size being used for adjustment than the "high gain" mode. As such, at step 966, the frequency may be increased by a small step, such as 50 Hz. Following step 966, the phase offset (and the impedance) of the nebulizer element may again be measured at step 930. If the phase delta is zero, no frequency adjustment may be necessary at step 966.

While a wide variety of drugs, liquids, liquid drugs, and drugs dissolved in liquid may be aerosolized, the following provides extensive examples of what may be aerosolized. Additional examples are provided in U.S. application Ser. No. 12/341,780, the entire disclosure of which is incorporated herein for all purposes. Nearly any anti-gram-negative, anti-gram-positive antibiotic, or combinations thereof may be used. Additionally, antibiotics may comprise those having broad spectrum effectiveness, or mixed spectrum effectiveness. Antifungals, such as polyene materials, in particular, amphotericin B are also suitable for use herein. Examples of anti-gram-negative antibiotics or salts thereof include, but are not limited to, aminoglycosides or salts thereof. Examples of aminoglycosides or salts thereof include gentamicin, amikacin, kanamycin, streptomycin, neomycin, netilmicin, paramecin, tobramycin, salts thereof, and combinations thereof. For instance, gentamicin sulfate is the sulfate salt, or a mixture of such salts, of the antibiotic substances produced by the growth of Micromonospora purpurea. Gentamicin sulfate, USP, may be obtained from Fujian Fukang Pharmaceutical Co., LTD, Fuzhou, China. Amikacin is typically supplied as a sulfate salt, and can be obtained, for example, from Bristol-Myers Squibb. Amikacin may include related substances such as kanamicin.

Examples of anti-gram-positive antibiotics or salts thereof include, but are not limited to, macrolides or salts thereof. Examples of macrolides or salts thereof include, but are not limited to, vancomycin, erythromycin, clarithromycin, azithromycin, salts thereof, and combinations thereof. For instance, vancomycin hydrochloride is a hydrochloride salt of vancomycin, an antibiotic produced by certain strains of *Amycolatopsis orientalis*, previously designated *Streptomyces orientalis*. Vancomycin hydrochloride is a mixture of related substances consisting principally of the monohydrochloride of vancomycin B. Like all glycopeptide antibiotics, vancomycin hydrochloride contains a central core heptapeptide. Vancomycin hydrochloride, USP, may be obtained from Alpharma, Copenhagen, Denmark.

In some embodiments, the composition comprises an antibiotic and one or more additional active agents. The additional active agent described herein includes an agent, drug, or compound, which provides some pharmacologic, often beneficial, effect. This includes foods, food supplements, nutrients, drugs, vaccines, vitamins, and other beneficial agents. As used herein, the terms further include any physiologically or pharmacologically active substance that produces a localized or systemic effect in a patient. An active agent for incorporation in the pharmaceutical formulation described herein may be an inorganic or an organic compound, including, without limitation, drugs which act on: the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autacoid systems, the alimentary and excretory systems, the histamine system, and the central nervous system.

Examples of additional active agents include, but are not limited to, anti-inflammatory agents, bronchodilators, and combinations thereof.

Examples of bronchodilators include, but are not limited to, β-agonists, anti-muscarinic agents, steroids, and combinations thereof. For instance, the steroid may comprise albuterol, such as albuterol sulfate.

Active agents may comprise, for example, hypnotics and sedatives, psychic energizers, tranquilizers, respiratory drugs, anticonvulsants, muscle relaxants, antiparkinson agents (dopamine antagnonists), analgesics, anti-inflammatories, antianxiety drugs (anxiolytics), appetite suppressants, antimigraine agents, muscle contractants, additional anti-infectives (antivirals, antifungals, vaccines) antiarthritics, antimalarials, antiemetics, anepileptics, cytokines, growth factors, anti-cancer agents, antithrombotic agents, antihypertensives, cardiovascular drugs, antiarrhythmics, antioxicants, anti-asthma agents, hormonal agents including contraceptives, sympathomimetics, diuretics, lipid regulating agents, antiandrogenic agents, antiparasitics, anticoagulants, neoplastics, antineoplastics, hypoglycemics, nutritional agents and supplements, growth supplements, antienteritis agents, vaccines, antibodies, diagnostic agents, and contrasting agents. The active agent, when administered by inhalation, may act locally or systemically.

The active agent may fall into one of a number of structural classes, including but not limited to small molecules, peptides, polypeptides, proteins, polysaccharides, steroids, proteins capable of eliciting physiological effects, nucleotides, oligonucleotides, polynucleotides, fats, electrolytes, and the like.

Examples of active agents suitable for use in this invention include but are not limited to one or more of calcitonin, amphotericin B, erythropoietin (EPO), Factor VIII, Factor IX, ceredase, cerezyme, cyclosporin, granulocyte colony stimulating factor (GCSF), thrombopoietin (TPO), alpha-1 proteinase inhibitor, elcatonin, granulocyte macrophage colony stimulating factor (GMCSF), growth hormone, human growth hormone (HGH), growth hormone releasing hormone (GHRH), heparin, low molecular weight heparin (LMWH), interferon alpha, interferon beta, interferon gamma, interleukin-1 receptor, interleukin-2, interleukin-1 receptor antagonist, interleukin-3, interleukin-4, interleukin-6, luteinizing hormone releasing hormone (LHRH), factor IX, insulin, pro-insulin, insulin analogues (e.g., mono-acylated insulin as described in U.S. Pat. No. 5,922,675, which is incorporated herein by reference in its entirety), amylin, C-peptide, somatostatin, somatostatin analogs including octreotide, vasopressin, follicle stimulating hormone (FSH), insulin-like growth factor (IGF), insulintropin, macrophage colony stimulating factor (M-CSF), nerve growth factor (NGF), tissue growth factors, keratinocyte growth factor (KGF), glial growth factor (GGF), tumor necrosis factor (TNF), endothelial growth factors, parathyroid hormone (PTH), glucagon-like peptide thymosin alpha 1, IIb/IIIa inhibitor, alpha-1 antitrypsin, phosphodiesterase (PDE) compounds, VLA-4 inhibitors, bisphosphonates, respiratory syncytial virus antibody, cystic fibrosis transmembrane regulator (CFTR) gene, deoxyreibonuclease (Dnase), bactericidal/permeability increasing protein (BPI), anti-CMV antibody, 1 3-cis retinoic acid, oleandomycin, troleandomycin, roxithromycin, clarithromycin, davercin, azithromycin, flurithromycin, dirithromycin, josamycin, spiromycin, midecamycin, leucomycin, miocamycin, rokitamycin, andazithromycin, and swinolide A; fluoroquinolones such as ciprofloxacin, ofloxacin, levofloxacin, trovafloxacin, alatrofloxacin, moxifloxicin, norfloxacin, enoxacin, grepafloxacin, gatifloxacin, lomefloxacin, sparfloxacin, temafloxacin, pefloxacin, amifloxacin, fleroxacin, tosufloxacin, prulifloxacin, irloxacin, pazufloxacin, clinafloxacin, and sitafloxacin, teicoplanin, rampolanin, mideplanin, colistin, daptomycin, gramicidin, colistimethate, polymixins such as polymixin B, capreomycin, bacitracin, penems; penicillins including penicllinase-sensitive agents like penicillin G, penicillin V, penicillinase-resistant agents like methicillin, oxacillin, cloxacillin, dicloxacillin, floxacillin, nafcillin; gram negative microorganism active agents like ampicillin, amoxicillin, and hetacillin, cillin, and galampicillin; antipseudomonal penicillins like carbenicillin, ticarcillin, azlocillin, mezlocillin, and piperacillin; cephalosporins like cefpodoxime, cefprozil, ceftbuten, ceftizoxime, ceftriaxone, cephalothin, cephapirin, cephalexin, cephradrine, cefoxitin, cefamandole, cefazolin, cephaloridine, cefaclor, cefadroxil, cephaloglycin, cefuroxime, ceforanide, cefotaxime, cefatrizine, cephacetrile, cefepime, cefixime, cefonicid, cefoperazone, cefotetan, cefinetazole, ceftazidime, loracarbef, and moxalactam, monobactams like aztreonam; and carbapenems such as imipenem, meropenem, pentamidine isethiouate, lidocaine, metaproterenol sulfate, beclomethasone diprepionate, triamcinolone acetamide, budesonide acetonide, fluticasone, ipratropium bromide, flunisolide, cromolyn sodium, ergotamine tartrate and where applicable, analogues, agonists, antagonists, inhibitors, and pharmaceutically acceptable salt forms of the above. In reference to peptides and proteins, the invention is intended to encompass synthetic, native, glycosylated, unglycosylated, pegylated forms, and biologically active fragments, derivatives, and analogs thereof.

Active agents for use in the invention further include nucleic acids, as bare nucleic acid molecules, vectors, associated viral particles, plasmid DNA or RNA or other nucleic acid constructions of a type suitable for transfection or transformation of cells, i.e., suitable for gene therapy including antisense. Further, an active agent may comprise live attenuated or killed viruses suitable for use as vaccines. Other useful drugs include those listed within the Physician's Desk Reference (most recent edition), which is incorporated herein by reference in its entirety.

The amount of antibiotic or other active agent in the pharmaceutical formulation will be that amount necessary to deliver a therapeutically or prophylactically effective amount of the active agent per unit dose to achieve the desired result. In practice, this will vary widely depending upon the particular agent, its activity, the severity of the condition to be treated, the patient population, dosing requirements, and the desired therapeutic effect. The composition will generally contain anywhere from about 1 wt % to about 99 wt %, such as from about 2 wt % to about 95 wt %, or from about 5 wt % to 85 wt %, of the active agent, and will also depend upon the relative amounts of additives contained in the composition. The compositions of the invention are particularly useful for active agents that are delivered in doses of from 0.001 mg/day to 100 mg/day, such as in doses from 0.01 mg/day to 75 mg/day, or in doses from 0.10 mg/day to 50 mg/day. It is to be understood that more than one active agent may be incorporated into the formulations described herein and that the use of the term "agent" in no way excludes the use of two or more such agents.

Generally, the compositions are free of excessive excipients. In one or more embodiments, the aqueous composition consists essentially of the anti-gram-negative antibiotic, such as amikacin, or gentamicin or both, and/or salts thereof and water.

Further, in one or more embodiments, the aqueous composition is preservative-free. In this regard, the aqueous composition may be methylparaben-free and/or propylparaben-free. Still further, the aqueous composition may be saline-free.

In one or more embodiments, the compositions comprise an anti-infective and an excipient. The compositions may comprise a pharmaceutically acceptable excipient or carrier which may be taken into the lungs with no significant adverse toxicological effects to the subject, and particularly to the lungs of the subject. In addition to the active agent, a pharmaceutical formulation may optionally include one or more pharmaceutical excipients which are suitable for pulmonary administration. These excipients, if present, are generally present in the composition in amounts sufficient to perform their intended function, such as stability, surface modification, enhancing effectiveness or delivery of the composition or the like. Thus, if present, excipient may range from about 0.01 wt % to about 95 wt %, such as from about 0.5 wt % to about 80 wt %, from about 1 wt % to about 60 wt %. Preferably, such excipients will, in part, serve to further improve the features of the active agent composition, for example by providing more efficient and reproducible delivery of the active agent and/or facilitating manufacturing. One or more excipients may also be provided to serve as bulking agents when it is desired to reduce the concentration of active agent in the formulation.

For instance, the compositions may include one or more osmolality adjuster, such as sodium chloride. For instance, sodium chloride may be added to solutions of vancomycin hydrochloride to adjust the osmolality of the solution. In one or more embodiments, an aqueous composition consists essentially of the anti-gram-positive antibiotic, such as vancomycin hydrochloride, the osmolality adjuster, and water.

Pharmaceutical excipients and additives useful in the present pharmaceutical formulation include but are not limited to amino acids, peptides, proteins, non-biological polymers, biological polymers, carbohydrates, such as sugars, derivatized sugars such as alditols, aldonic acids, esterified sugars, and sugar polymers, which may be present singly or in combination.

Exemplary protein excipients include albumins such as human serum albumin (HSA), recombinant human albumin (rHA), gelatin, casein, hemoglobin, and the like. Suitable amino acids (outside of the dileucyl-peptides of the invention), which may also function in a buffering capacity, include alanine, glycine, arginine, betaine, histidine, glutamic acid, aspartic acid, cysteine, lysine, leucine, isoleucine, valine, methionine, phenylalanine, aspartame, tyrosine, tryptophan, and the like. Preferred are amino acids and polypeptides that function as dispersing agents. Amino acids falling into this category include hydrophobic amino acids such as leucine, valine, isoleucine, tryptophan, alanine, methionine, phenylalanine, tyrosine, histidine, and proline.

Carbohydrate excipients suitable for use in the invention include, for example, monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol), pyranosyl sorbitol, myoinositol and the like.

The pharmaceutical formulation may also comprise a buffer or a pH adjusting agent, typically a salt prepared from an organic acid or base. Representative buffers comprise organic acid salts of citric acid, ascorbic acid, gluconic acid, carbonic acid, tartaric acid, succinic acid, acetic acid, or phthalic acid, Tris, tromethamine hydrochloride, or phosphate buffers.

The pharmaceutical formulation may also include polymeric excipients/additives, e.g., polyvinylpyrrolidones, celluloses and derivatized celluloses such as hydroxymethylcellulose, hydroxyethylcellulose, and hydroxypropylmethylcellulose, Ficolls (a polymeric sugar), hydroxyethylstarch, dextrates (e.g., cyclodextrins, such as 2-hydroxypropyl-.beta.-cyclodextrin and sulfobutylether-.beta.-cyclodextrin), polyethylene glycols, and pectin.

The pharmaceutical formulation may further include flavoring agents, taste-masking agents, inorganic salts (for example sodium chloride), antimicrobial agents (for example benzalkonium chloride), sweeteners, antioxidants, antistatic agents, surfactants (for example polysorbates such as "TWEEN 20" and "TWEEN 80"), sorbitan esters, lipids (for example phospholipids such as lecithin and other phosphatidylcholines, phosphatidylethanolamines), fatty acids and fatty esters, steroids (for example cholesterol), and chelating agents (for example EDTA, zinc and other such suitable cations). Other pharmaceutical excipients and/or additives suitable for use in the compositions according to the invention are listed in "Remington: The Science & Practice of Pharmacy", 19.sup.th ed., Williams & Williams, (1995), and in the "Physician's Desk Reference", 52.sup.nd ed., Medical Economics, Montvale, N.J. (1998), both of which are incorporated herein by reference in their entireties.

It should be noted that the methods, systems, and devices discussed above are intended merely to be examples. It must be stressed that various embodiments may omit, substitute, or add various procedures or components as appropriate. For instance, it should be appreciated that, in alternative embodiments, the methods may be performed in an order different from that described, and that various steps may be added, omitted, or combined. Also, features described with respect to certain embodiments may be combined in various other embodiments. Different aspects and elements of the embodiments may be combined in a similar manner. Also, it should be emphasized that technology evolves and, thus, many of the elements are examples and should not be interpreted to limit the scope of the invention.

Specific details are given in the description to provide a thorough understanding of the embodiments. However, it will be understood by one of ordinary skill in the art that the embodiments may be practiced without these specific details. For example, well-known processes, algorithms, structures, and techniques have been shown without unnecessary detail in order to avoid obscuring the embodiments. This description provides example embodiments only, and is not intended to limit the scope, applicability, or configuration of the invention. Rather, the preceding description of the embodiments will provide those skilled in the art with an enabling description for implementing embodiments of the invention. Various changes may be made in the function and arrangement of elements without departing from the spirit and scope of the invention.

Further, the preceding description generally details aerosolizing liquid drugs. However, it should be understood that liquids besides liquid drugs may be aerosolized using similar devices and methods.

Also, it is noted that the embodiments may be described as a process which is depicted as a flow diagram or block diagram. Although each may describe the operations as a sequential process, many of the operations can be performed in parallel or concurrently. In addition, the order of the operations may be rearranged. A process may have additional steps not included in the figure.

What is claimed is:

1. A nebulizer system, the nebulizer system comprising:
   a liquid reservoir that is adapted to hold a liquid that is to be atomized;
   a nebulizer, comprising a nebulizer element having a plurality of apertures, wherein:
      the nebulizer element is configured to vibrate to atomize the liquid drained from the liquid reservoir; and
      the nebulizer element is driven by a drive signal;
   a driver that outputs the drive signal, the driver comprising:
      a frequency generator;
      a phase shift detector configured to measure a phase offset of the drive signal, wherein
         the phase offset indicates a phase difference between a voltage of the drive signal and a current of the drive signal;
      a processor configured to:
         determine a phase delta, wherein:
            the phase delta indicates a difference between a target phase offset and the measured phase offset, and
            the target phase offset indicates a non-zero target phase difference between the voltage of the drive signal and the current of the drive signal;
         change a frequency of the drive signal that is output by the frequency generator to decrease the phase delta; and
         adjust a voltage magnitude of the drive signal in response to the frequency of the drive signal being increased, the adjusted voltage magnitude compensating for an increased flow rate caused by a negative bias pressure developing within the liquid reservoir, wherein the driver outputs the drive signal to the nebulizer element, the drive signal having the changed frequency and the adjusted voltage magnitude.

2. The nebulizer system of claim 1, wherein the processor being configured to change the frequency of the drive signal that is output by the frequency generator to decrease the phase delta comprises the processor being configured to:
   change the frequency of the drive signal that is output by the frequency generator to decrease the phase delta to less than a threshold phase delta in a high gain mode;
   determine the phase delta is less than the threshold phase delta; and
   at least partially in response to determining the phase delta is less than the threshold phase delta, change the frequency of the drive signal that is output by the frequency generator to decrease the phase delta in a low gain mode, wherein
      the low gain mode results in a smaller frequency change than the high gain mode.

3. The nebulizer system of claim 2, wherein the processor is further configured to:
   calculate an impedance of the nebulizer element, wherein
      the processor changing the frequency of the drive signal that is output by the frequency generator in the low gain mode is conditioned on the impedance of the nebulizer element being below an impedance threshold.

4. The nebulizer system of claim 2, wherein the processor is further configured to:
   determine a slope of the phase offset, wherein
      the processor changing the frequency of the drive signal that is output by the frequency generator in the low gain mode is conditioned on the slope of the phase offset being negative.

5. The nebulizer system of claim 2, wherein the threshold phase delta is five degree or less.

6. The nebulizer system of claim 1, wherein the target phase offset between the voltage of the drive signal and the current of the drive signal is between 25 degrees and 35 degrees.

7. The nebulizer system of claim 6, wherein the target phase offset between the voltage of the drive signal and the current of the drive signal is 30 degrees.

8. The nebulizer system of claim 1, wherein energizing the nebulizer element of the nebulizer with the drive signal causes the liquid to be atomized.

9. The nebulizer system of claim 8, wherein the liquid is a medicine.

10. The nebulizer system of claim 1, wherein the processor is further configured to limit adjustment of the voltage magnitude by a threshold rate such that the voltage magnitude is not decreased at a rate greater than the threshold rate.

11. The nebulizer system of claim 1, wherein the processor is further configured to:
    determine the phase delta has been less than a threshold value for at least a threshold period of time; and
    in response to determining the amount of error has been less than the threshold value for at least the period of time, store a current frequency of the drive signal as output by the frequency generator as a lock-in frequency.

12. The nebulizer system of claim 1, wherein the processor is further configured to:
    determine that a present frequency of the drive signal is greater than the lock-in frequency; and
    in response to determining that the present frequency of the drive signal is greater than the lock-in frequency, scale down the magnitude of the drive signal by a stored decay rate such that a rate of change of the drive signal is limited by a stored threshold rate.

13. A method for using a nebulizer system, the method comprising:
    storing, in a liquid reservoir of the nebulizer system, a liquid to be atomized;
    energizing, by a driver of the nebulizer system, a nebulizer element using a drive signal, wherein:

a frequency generator of the driver is used to create a frequency of the drive signal; and the nebulizer element is configured to vibrate to atomize the liquid from the liquid reservoir and the nebulizer element comprises a plurality of apertures;

measuring, by a phase shift detector of the driver of the nebulizer system, a phase offset of the drive signal;

determining, by the driver, a phase delta of drive signal, wherein:

the phase delta indicates a difference between a target phase offset and the measured phase offset, and the target phase offset indicates a non-zero target phase difference between the voltage of the drive signal and the current of the drive signal;

changing, by the driver of the nebulizer system, the frequency of the drive signal that is output by the frequency generator to decrease the phase delta; and adjusting, by the driver of the nebulizer system, a voltage magnitude of the drive signal in response to the frequency of the drive signal being increased.

14. The method for using the nebulizer system of claim 13, wherein changing the frequency of the drive signal that is output comprises:

changing the frequency of the drive signal that is output by the frequency generator to decrease the phase delta to less than a threshold phase delta in a high gain mode;

determining the phase delta is less than the threshold phase delta; and at least partially in response to determining the phase delta is less than the threshold phase delta, changing the frequency of the drive signal that is output by the frequency generator to decrease the phase delta in a low gain mode, wherein the low gain mode results in a smaller frequency change than the high gain mode.

15. The method for using the nebulizer system of claim 13, wherein the processor is further configured to:

calculating, by the driver, an impedance of the nebulizer element, wherein changing the frequency of the drive signal in the low gain mode is conditioned on the impedance of the nebulizer element being below an impedance threshold.

16. The method for using the nebulizer system of claim 13, further comprising:

determining, by the driver, a slope of the phase offset, wherein changing the frequency of the drive signal in the low gain mode is conditioned on the slope of the phase offset being negative.

17. The method for using the nebulizer system of claim 14, wherein the threshold phase delta is five degree or less.

18. The method for using the nebulizer system of claim 13, wherein the target phase offset between the voltage of the drive signal and the current of the drive signal is between 25 degrees and 35 degrees.

19. The method for using the nebulizer system of claim 18, wherein the target phase offset between the voltage of the drive signal and the current of the drive signal is 30 degrees.

20. The method for using the nebulizer system of claim 13, wherein energizing the nebulizer element of the nebulizer with the drive signal causes the liquid to be atomized.

21. The method for using the nebulizer system of claim 20, wherein the liquid is a medicine.

* * * * *